(12) United States Patent
Fischer et al.

(10) Patent No.: US 7,595,404 B2
(45) Date of Patent: Sep. 29, 2009

(54) THIAZOLYL-SUBSTITUTED CARBOCYCLIC 1,3-DIONES AS PESTICIDAL AGENTS

(75) Inventors: Reiner Fischer, Monheim (DE); Astrid Ullmann, Köln (DE); Axel Trautwein, Bergisch Gladbach (DE); Mark Wilhelm Drewes, Langenfeld (DE); Christoph Erdelen, Leichlingen (DE); Angelika Lubos-Erdelen, legal representative, Leichlingen (DE); Peter Dahmen, Neuss (DE); Dieter Feucht, Monheim (DE); Rolf Pontzen, Leichlingen (DE); Karl-Heinz Kuck, Langenfeld (DE); Ulrike Wachendorff-Neumann, Neuwied (DE)

(73) Assignee: Bayer CropScience AG, Monheim (DE)

( * ) Notice: Subject to any disclaimer, the term of this patent is extended or adjusted under 35 U.S.C. 154(b) by 564 days.

(21) Appl. No.: 10/474,308

(22) PCT Filed: Apr. 2, 2002

(86) PCT No.: PCT/EP02/03620

§ 371 (c)(1),
(2), (4) Date: Oct. 27, 2004

(87) PCT Pub. No.: WO02/088098

PCT Pub. Date: Nov. 7, 2002

(65) Prior Publication Data

US 2007/0135630 A1 Jun. 14, 2007

(30) Foreign Application Priority Data

Apr. 12, 2001 (DE) .................. 101 18 310

(51) Int. Cl.
*C07D 275/03* (2006.01)
*A61K 31/381* (2006.01)

(52) U.S. Cl. ...................... 548/214; 614/369

(58) Field of Classification Search .................. 548/214
See application file for complete search history.

(56) References Cited

U.S. PATENT DOCUMENTS

| 3,538,107 A | 11/1970 | Hepworth et al. ........... 260/302 |
| 3,749,787 A | 7/1973 | Hepworth et al. ........... 424/270 |
| 4,659,372 A | 4/1987 | Wheeler ...................... 71/106 |
| 4,725,610 A | 2/1988 | Meguro et al. .............. 514/369 |

FOREIGN PATENT DOCUMENTS

EP 03 685 92 5/1990

OTHER PUBLICATIONS

RN 128797-82-0, retrieved from CAPLUS and retrieved on Aug. 28, 2008.*

* cited by examiner

*Primary Examiner*—Rebecca L Anderson
*Assistant Examiner*—Shawquia Young
(74) *Attorney, Agent, or Firm*—Raymond J. Harmuth; Richard E. L. Henderson

(57) ABSTRACT

The present invention relates to novel hetaryl-substituted carbocyclic 1,3-diones of the Formula (I)

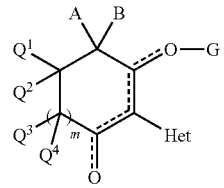

in which
A, B, $Q^1$, $Q^2$, $Q^3$, $Q^4$, G, m and Het are as defined in the description,
to a plurality of processes for their preparation and to their use as pesticides, herbicides and fungicides.

9 Claims, No Drawings

THIAZOLYL-SUBSTITUTED CARBOCYCLIC 1,3-DIONES AS PESTICIDAL AGENTS

The present invention relates to novel hetaryl-substituted cyclopentane- and cyclohexane-1,3-dione derivatives, to a plurality of processes for their preparation and to their use as bioactive compounds in agriculture.

2-(2-Amino-thiazol-4-yl)-3-hydroxy-5,5-dimethyl-cyclohex-2-enone is known;

Pshenichnyi, V. N. et al; CNClALi; Chem. Heterocycl. Compd. (Engl. transl.) EN; 26, 1175-1178 (1990).

This invention now provides novel compounds of the formula (I)

(I)

in which

Het represents a nitrogen-containing 5-membered heterocycle, preferably from the group consisting of thiazolyl, which heterocycle is optionally substituted by halogen, alkyl, alkoxy, alkenyloxy, halogenoalkyl, halogenoalkoxy, halogenoalkenyloxy, cyano, nitro, alkylthio, alkylsulphinyl, alkylsulphonyl, optionally substituted phenyl or phenoxy, m represents the number 0 or 1, A represents hydrogen, represents in each case optionally halogen-substituted alkyl, alkenyl, alkoxyalkyl, polyalkoxyalkyl, alkylthioalkyl, saturated or unsaturated, optionally substituted cycloalkyl in which optionally at least one ring atom is replaced by a heteroatom, or in each case optionally halogen-, alkyl-, halogenoalkyl-, alkoxy-, halogenoalkoxy-, cyano- or nitro-substituted aryl, arylalkyl or hetaryl, B represents hydrogen or alkyl, A and B together with the carbon atom to which they are attached represent a saturated or unsaturated, unsubstituted or substituted cycle which optionally contains at least one heteroatom, A and $Q^1$ together represent optionally substituted alkanediyl in which two not directly adjacent carbon atoms optionally form a further optionally substituted cycle, $Q^1$ represents hydrogen, alkyl, alkoxyalkyl, optionally substituted cycloalkyl (in which optionally one methylene group is replaced by oxygen or sulphur) or in each case optionally substituted phenyl, hetaryl, phenylalkyl or hetarylalkyl, $Q^2$, $Q^3$, $Q^4$ independently of one another represent hydrogen or alkyl, $Q^1$ and $Q^2$ together with the carbon atom to which they are attached represent a saturated or unsaturated, unsubstituted or substituted cycle which optionally contains one heteroatom, G represents hydrogen (a) or represents one of the groups (b)

(c)

(d)

(e)

(f)

(g)

in which

E represents a metal ion or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$ represents in each case optionally substituted alkyl, halogenoalkyl, phenyl or benzyl, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur.

Depending inter alia on the nature of the substituents, the compounds of the formula (I) can be present as geometrical and/or optical isomers or isomer mixtures of varying composition which, if desired, can be separated in a known manner. The present invention provides both the pure isomers and the isomer mixtures, their preparation and use and the compositions comprising them. However, hereinbelow, for the sake of simplicity, only compounds of the formula (I) are referred to, although this includes both the pure compounds and, if appropriate, mixtures having varying proportions of isomeric compounds.

Depending on the position of the substituent G, the compounds of the formula (I) can be present in the two isomeric forms of the formulae (I-α) and (I-β), (I-α)

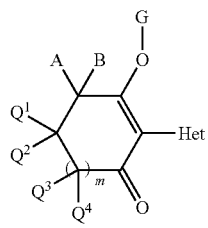

(I-β)

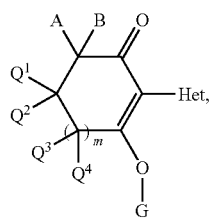

which is meant to be expressed by the broken line in the formula (I).

The compounds of the formulae (I-α) and (I-β) can be present either as mixtures or else in the form of their pure isomers. Mixtures of the compounds of the formulae (I-α) and (I-β) can, if desired, be separated in a manner known per se by physical methods, for example by chromatographic methods.

For reasons of clarity, in each case only one of the possible isomers is shown hereinbelow. This does not preclude that the compounds are, if appropriate, present in the form of the isomer mixtures or in the respective other isomeric form.

Including Het for thiazolyl and m for the numbers 0 and 1, the following principal structures (I-1) and (I-2) result (I-1)

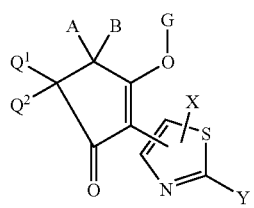

(I-2)

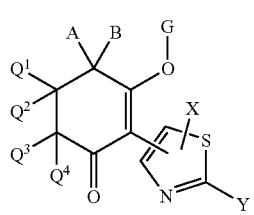

Including the different meanings (a), (b), (c), (d,(e), (f) and (g) of the group G. the following principal structures (I-1-a) to (I-1-g) result if m represents the number 0 (I-1), (I-1-a)

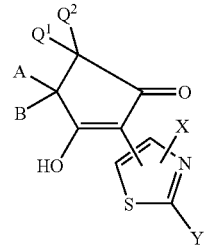

(I-1-b)

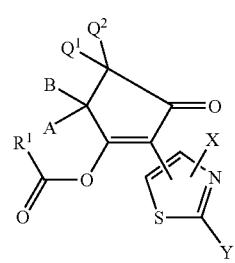

(I-1-c)

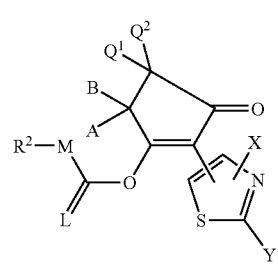

(I-1-d)

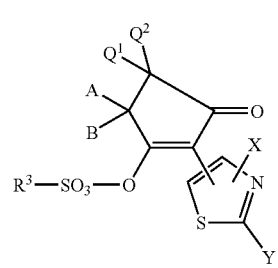

(I-1-e)

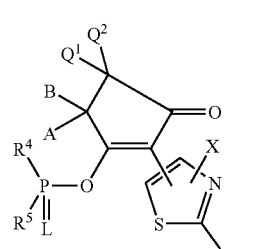

(I-1-f)

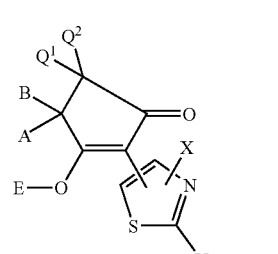

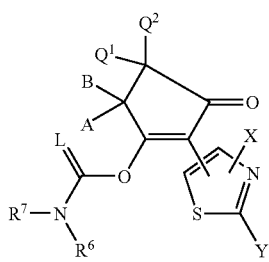

(I-1-g)

in which

A, B, E, L, M, $Q^1$, $Q^2$, $R^1$, $R^2$, $R^3$, $R^4$, $R^5$, $R^6$ and $R^7$ are as defined above, and x represents hydrogen, halogen, alkyl, alkoxy, alkenyloxy, nitro, cyano or optionally substituted phenyl and Y represents halogen, alky, halogenoalkyl, alkoxy, halogenoalkoxy or in each case optionally substituted phenyl or phenoxy.

Including the different meanings (a), (b), (c), (d), (e), (f) and (g) of the group G, the following principal structures (I-2-a) to (I-2-g) result if m represents the number 1 (I-2), (I-2-a):

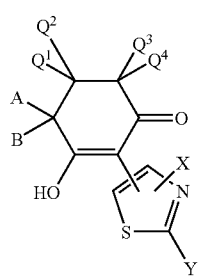

(I-2-b):

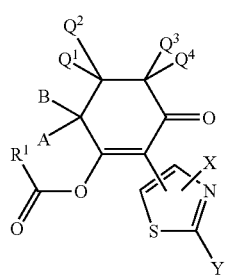

(I-2-c):

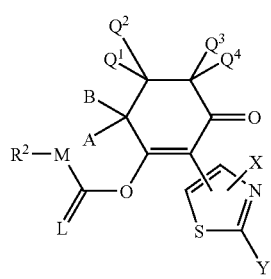

(I-2-d):

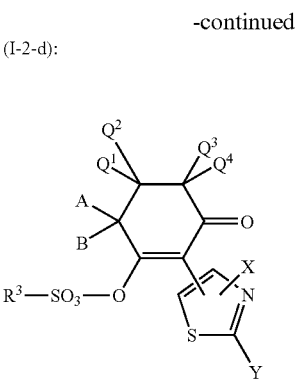

(I-2-e):

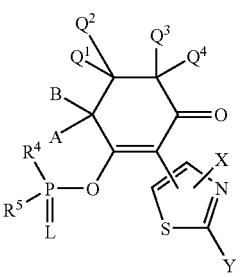

(I-2-f):

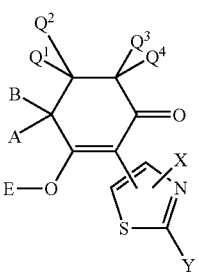

(I-1-g):

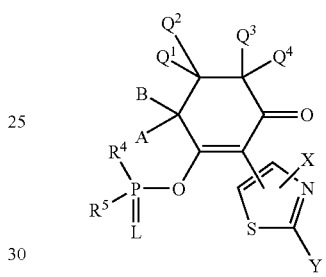

in which

A, B, E, L, M, $Q^1$, $Q^2$, $Q^3$, $Q^4$, X, Y, $R^1$, $R^2$, $R^3$, $R^4$, $R^5$, $R^6$ and $R^7$ are as defined above.

Furthermore, it has been found that the novel compounds of the formula (I) are obtained by one of the processes described below:

(A) substituted cyclopentane-1,3-diones or their enoles of the formula (I-1-a)

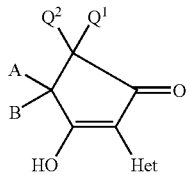
(I-1-a)

in which
A, B, $Q^1$, $Q^2$ and Het are as defined above,
are obtained when
ketocarboxylic esters of the formula (II)

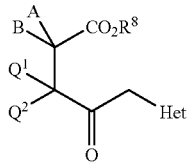
(II)

in which
A, B, $Q^1$, $Q^2$ and Het are as defined above and
$R^8$ represents alkyl (preferably $C_1$-$C_6$-alkyl)
are condensed intramolecularly, if appropriate in the presence of a diluent and in the presence of a base.

Furthermore, it has been found
(B) that substituted cyclohexane-1,3-diones of the formula (1-2-a)

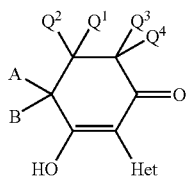
(I-2-a)

in which
A, B, $Q^1$, $Q^2$, $Q^3$, $Q^4$, and Het are as defined above
are obtained when
ketocarboxylic esters of the formula (III)

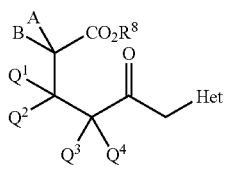
(III)

in which
A, B. $Q^1$, $Q^2$, $Q^3$, $Q^4$, and Het are as defined above, and
$R^8$ represents alkyl (preferably $C_1$-$C_6$-alkyl)
are condensed intramolecularly in the presence of a diluent and in the presence of a base.

Furthermnore, it has been found
(C) that the compounds of the formulae (I-1-b) to (I-2-b) shown above in which A, B, $Q^1$, $Q^2$, $Q^3$, $Q^4$, m, $R^1$ and Het are as defined above are obtained when compounds of the formulae (I-1-a) to (I-2-a) shown above in which A, B, $Q^1$, $Q^2$, $Q^3$, $Q^4$, m and Het are as defined above are in each case
(α) reacted with acid halides of the formula (IV)

(IV)

in which
$R^1$ is as defined above and
Hal represents halogen (in particular chlorine or bromine)
or
(β) reacted with carboxylic anhydrides of the formula (V)

$R^1$—CO—O—CO—$R^1$ (V)

in which
$R^1$ is as defined above,
if appropriate in the presence of a diluent and if appropriate in the presence of an acid binder;
(D) that the compounds of the formulae (I-1-c) to (I-2-c) shown above in which A, B, $Q^1$, $Q^2$, $Q^3$, $Q^4$, m, $R^2$, M and Het are as defined above and L represents oxygen are obtained when compounds of the formulae (I-1-a) to (I-2-a) shown above in which A, B, $Q^1$, $Q^2$, $Q^3$, $Q^4$, m and Het are as defined above are in each case
reacted with chloroformic esters or chloroformic thioesters of the formula (VI)

$R^2$-M-CO—Cl (VI)

in which
$R^2$ and M are as defined above,
if appropriate in the presence of a diluent and if appropriate in the presence of an acid binder;
(E) that compounds of the formulae (I-1-c) to (I-2-c) shown above in which A, B, $Q^1$, $Q^2$, $Q^3$, $Q^4$, m, $R^2$, M and Het are as defined above and L represents sulphur are obtained when compounds of the formulae (I-1-a) to (I-2-a) shown above in which A, B, $Q^1$, $Q^2$, $Q^3$, $Q^4$, m and Het are as defined above are in each case
reacted with chloromonothioformic esters or chlorodithioformic esters of the formula (VII)

(VII)

in which
M and $R^2$ are as defined above,
if appropriate in the presence of a diluent and if appropriate in the presence of an acid binder and
(F) that compounds of the formulae (I-1-d) to (I-2-d) shown above in which A, B, $Q^1$, $Q^2$, $Q^3$, $Q^4$, m, $R^3$ and Het are as defined above are obtained when compounds of the formulae (I-1-a) and (I-2-a) shown above in which A, B, $Q^1$, $Q^2$, $Q^3$, $Q^4$, m and Het are as defined above are in each case
reacted with sulphonyl chlorides of the formula (VIII)

$R^3$—$SO_2$—Cl (VIII)

in which

R³ is as defined above, if appropriate in the presence of a diluent and if appropriate in the presence of an acid binder, (G) that compounds of the formulae (I-1-e) to (I-2-e) shown above in which A, B, L, Q¹, Q², Q³, Q⁴, m, R⁴, R⁵ and Het are as defined above are obtained when compounds of the formulae (I-1-a) to (I-2-a) shown above in which A, B, Q¹, Q², Q³, Q⁴, m and Het are as defined above are in each case reacted with phosphorus compounds of the formula (IX)

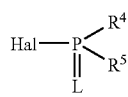
(IX)

in which

L, R⁴ and R⁵ are as defined above and

Hal represents halogen (in particular chlorine or bromine), if appropriate in the presence of a diluent and if appropriate in the presence of an acid binder, (H) that compounds of the formulae (I-1-f) to (I-2-f) shown above in which A, B, E, Q¹, Q², Q³, Q⁴, m and Het are as defined above are obtained when compounds of the formulae (I-1-a) to (I-2-a) in which A, B, Q¹, Q², Q³, Q⁴, m and Het are as defined above are in each case reacted with metal compounds or amines of the formulae (X) and (XI), respectively, Me(OR¹¹)_t  (X)

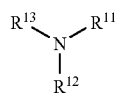
(XI)

in which

Me represents a mono- or divalent metal (preferably an alkali metal or alkaline earth metal such as lithium, sodium, potassium, magnesium or calcium), t represents the number 1 or 2 and R¹¹, R¹², R¹³ independently of one another represent hydrogen or alkyl (preferably C₁-C₈-alkyl), if appropriate in the presence of a diluent, (I) that compounds of the formulae (I-1-g) to (I-2-g) shown above in which A, B, L, Q¹, Q², Q³, Q⁴, Q⁴, m, R⁶, R⁷ and Het are as defined above are obtained when compounds of the formulae (I-1-a) to (I-2-a) shown above in which A, B, Q¹, Q², Q³, Q⁴, m and Het are as defined above are in each case (α) reacted with isocyanates or isothiocyanates of the formula (XII)

R⁶—N═C═L  (XII)

in which

R⁶ and L are as defined above, if appropriate in the presence of a diluent and if appropriate in the presence of a catalyst, or (β) reacted with carbamoyl chlorides or thiocarbamoyl chlorides of the formula (XII)

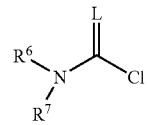
(XIII)

in which

L, R⁶ and R⁷ are as defined above, if appropriate in the presence of a diluent and if appropriate in the presence of an acid binder.

Furthermore, it has been found that the novel compounds of the formula (I) have, depending on the substituents, very good activity both as pesticides, preferably as insecticides and acaricides, and as herbicides and fungicides.

The formula (I) provides a general definition of the compounds according to the invention. Preferred substituents or ranges of the radicals given in the formulae mentioned above and below are illustrated below:

Het preferably represents

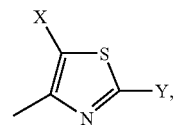

m preferably represents the number 0 or 1,

X preferably represents hydrogen, halogen, C₁-C₆-alkyl, C₁-C₆-alkoxy, C₃-C₆-alkenyloxy, nitro or cyano, Y preferably represents halogen, C₁-C₆-alkyl, C₁-C₆-halogenoalkyl, C₁-C₆-alkoxy, C₁-C₆-halogenoalkoxy or represents the groups

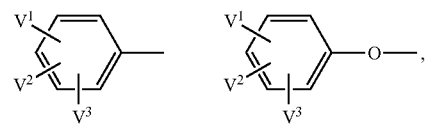

V¹ preferably represents hydrogen, halogen, C₁-C₁₂-alkyl, C₁-C₆-alkoxy, C₁-C₆-alkylthio, C₁-C₆-alkylsulphinyl, C₁-C₆-alkylsulphonyl, C₁-C₄-halogenoalkyl, C₁-C₄-halogenoalkoxy, nitro, cyano or represents phenyl, phenoxy, phenoxy-C₁-C₄-alkyl, phenyl-C₁-C₄-alkoxy, phenylthio-C₁-C₄-alkyl or phenyl-C₁-C₄-alkylthio, each of which is optionally mono- or polysubstituted by halogen, C₁-C₆-alkyl, C₁-C₆-alkoxy, C₁-C₄-halogenoalkyl, C₁-C₄-halogenoalkoxy, nitro or cyano, V² and V³ independently of one another preferably represent hydrogen, halogen, C₁-C₆-alkyl, C₁-C₆-alkoxy, C₁-C₄-halogenoalkyl or C₁-C₄-halogenoalkoxy, V¹ and V² jointly together with the carbon atoms to which they are attached preferably represent an optionally C₁-C₄-alkyl- or halogen-substituted 5- or 6-membered cycle in which optionally one or two carbon atoms may be replaced by oxygen, sulphur or nitrogen, A preferably represents hydrogen or in each case optionally halogen-substituted C₁-C₁₂-alkyl, C₃-C₈-alkenyl, C₁-C₆-alkoxy-C₁-C₄-alkyl, optionally halogen-, C₁-C₄-alkyl- or C₁-C₄-alkoxy-substituted C₃-C₈-cycloalkyl or C₃-C₆-cycloalkyl-$C_1$-$C_4$-alkyl, in which optionally one or two not directly adjacent ring members are replaced by oxygen and/or sulphur, or represents in each case optionally halogen-, $C_1$-$C_6$-alkyl-, $C_1$-$C_6$-halogenoalkyl-, $C_1$-$C_6$-alkoxy-, $C_1$-$C_6$-halogenoalkoxy-, cyano- or nitro-substituted phenyl, benzyl, hetaryl having 5 or 6 ring atoms (for example furanyl, pyridyl, imidazolyl, triazolyl, pyrazolyl, pyrimidyl, thiazolyl or thienyl) or hetaryl-$C_1$-$C_4$-alkyl having 5 or 6 ring atoms (for example pyridyl-, pyrimidyl- or thiazolyl-$C_1$-$C_4$-alkyl), B preferably represents hydrogen or $C_1$-$C_6$-alkyl, A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_6$-alkyl, $C_3$-$C_8$-cycloalkyl, $C_1$-$C_6$-halogenoalkyl, $C_1$-$C_6$-alkoxy, $C_1$-$C_6$-alkylthio, halogen or phenyl, A and $Q^1$ together preferably represent $C_3$-$C_6$-alkanediyl which is optionally mono- or disubstituted by identical or different substituents from the group consisting of $C_1$-$C_4$-alkyl and $C_1$-$C_4$-alkoxy, $Q^1$ preferably represents hydrogen, $C_1$-$C_6$-alkyl, $C_1$-$C_6$-alkoxy-$C_1$-$C_2$-alkyl, optionally fluorine-, chlorine-, $C_1$-$C_4$-alkyl-, $C_1$-$C_2$-halogenoalkyl- or $C_1$-$C_4$-alkoxy-substituted $C_3$-$C_8$-cycloalkyl in which optionally one methylene group is replaced by oxygen or sulphur or in each case optionally halogen-, $C_1$-$C_4$-alkyl-, $C_1$-$C_4$-alkoxy-, $C_1$-$C_2$-halogenoalkyl-, $C_1$-$C_2$-halogenoalkoxy-, cyano- or nitro-substituted phenyl, pyridyl, thienyl, thiazolyl, phenyl-$C_1$-$C_4$-alkyl, pyridyl -$C_{11}$-$C_2$-alkyl or thiazolyl-$C_1$-$C_2$-alkyl, $Q^2$, $Q^3$, $Q^4$ independently of one another preferably represent hydrogen or $C_1$-$C_4$-alkyl, $Q^1$ and $Q^2$ together with the carbon atom to which they are attached preferably represent optionally $C_1$-$C_6$-alkyl-, $C_1$-$C_6$-alkoxy- or $C_1$-$C_2$-halogenoalkyl-substituted $C_3$-$C_7$-cycloalkyl in which optionally one ring member is replaced by oxygen or sulphur, G preferably represents hydrogen (a) or represents one of the groups

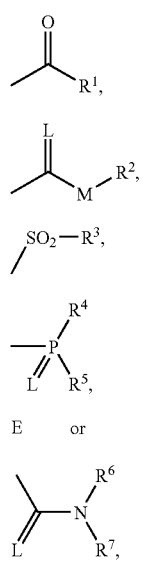

in particular (a), (b), (c) or (g), in which

E represents a metal ion or an ammonium ion,

L represents oxygen or sulphur and

M represents oxygen or sulphur, $R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl, in which optionally one or more (preferably one or two) not directly adjacent ring members are replaced by oxygen and/or sulphur, represents optionally halogen-, cyano-, nitro-, $C_1$-$C_6$-alkyl, $C_1$-$C_6$-alkoxy-, $C_1$-$C_6$-halogenoalkyl-, $C_1$-$C_6$-halogenoalkoxy-, $C_1$-$C_6$-alkylthio or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-halogenoalkyl- or $C_1$-$C_6$-halogenoalkoxy-substituted phenyl-$C_1$-$C_6$-alkyl, represents optionally halogen-, $C_1$-$C_6$-alkyl- or trifluoromethyl-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy- $C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-halogenoalkyl- or $C_1$-$C_6$-halogenoalkoxy-substituted phenyl or benzyl, $R^3$ preferably represents optionally halogeno-substituted $C_1$-$C_8$-alkyl or represents in each case optionally halogen-, $C_1$-$C_6$-alkyl-, $C_1$-$C_6$-alkoxy-, $C_1$-$C_4$-halogenoalkyl-, $C_1$-$C_4$-halogenoalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkyl- or $C_1$-$C_4$-halogenoalkyl-substituted phenyl, benzyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-halogenoalkyl-, $C_1$-$C_8$-alkyl- or $C_1$-$C_8$-alkoxy-substituted phenyl, optionally halogen-, $C_1$-$C_8$-alkyl-, $C_1$-$C_8$-halogenoalkyl- or $C_1$-$C_8$-alkoxy-substituted benzyl or together with the nitrogen to which they are attached represent an optionally $C_1$-$C_4$-alkyl-substituted $C_3$-$C_6$-alkylene radical in which optionally one carbon atom is replaced by oxygen or sulphur.

In the radical definitions mentioned as being preferred, halogen represents fluorine, chlorine, bromine and iodine, in particular fluorine and chlorine, also as substituent, such as, for example, in halogenoalkyl.

Het particularly preferably represents

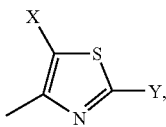

m particularly preferably represents the number 0 or 1,
X particularly preferably represents hydrogen, chlorine, bromine or $C_1$-$C_4$-alkyl,
Y particularly preferably represents chlorine, bromine, $C_1$-$C_4$-alkyl, $C_1$-$C_4$-halogenoalkyl, $C_1$-$C_4$-alkoxy, $C_1$-$C_4$-halogenoalkoxy or the group

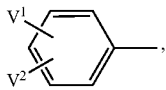

$V^1$ particularly preferably-represents hydrogen, fluorine, chlorine, $C_1$-$C_6$-alkyl, $C_1$-$C_4$-alkoxy, $C_1$-$C_2$-halogenoalkyl, $C_1$-$C_2$-halogenoalkoxy, nitro, cyano or phenoxy which is optionally mono- or disubstituted by fluorine, chlorine, bromine, $C_1$-$C_4$-alkyl, $C_1$-$C_4$-alkoxy, $C_1$-$C_2$-halogenoalkyl, $C_1$-$C_2$-halogenoalkoxy, nitro or cyano,
$V^2$ particularly preferably represents hydrogen, fluorine, chlorine, bromine, $C_1$-$C_4$-alkyl, $C_1$-$C_4$-alkoxy, $C_1$-$C_2$-halogenoalkyl or $C_1$-$C_2$-halogenoalkoxy,
$V^1$ and $V^2$ jointly, together with the carbon atoms to which they are attached, particularly preferably represent an optionally fluorine- or methyl-substituted 5- or 6-membered cycle in which optionally one or two carbon atoms may be replaced by oxygen,
A particularly preferably represents hydrogen, represents $C_1$-$C_8$-alkyl or $C_1$-$C_4$-alkoxy-$C_1$-$C_2$-alkyl, each of which is optionally mono- to trisubstituted fluorine, represents $C_5$-$C_6$-cycloalkyl or $C_3$-$C_6$-cycloalkyl-$C_1$-$C_2$-alkyl in which optionally one ring member is replaced by oxygen or sulphur, each of which radicals is optionally mono- or disubstituted by fluorine, chlorine, methyl, ethyl or methoxy, or represent phenyl or benzyl, each of which is optionally mono- or disubstituted by fluorine, chlorine, bromine, $C_1$-$C_4$-alkyl, $C_1$-$C_2$-halogenoalkyl, $C_1$-$C_4$-alkoxy or $C_1$-$C_2$-halogenoalkoxy,
B particularly preferably represents hydrogen or $C_1$-$C_4$-alkyl,
A, B and the carbon atom to which they are attached particularly preferably represent saturated $C_5$-$C_6$-cycloalkyl in which optionally one ring member is replaced by oxygen and which is optionally monosubstituted by $C_1$-$C_4$-alkyl, trifluoromethyl or $C_1$-$C_4$-alkoxy,
with the proviso that in this case $Q^1$ represents only hydrogen or $C_1$-$C_4$-alkyl,
A and $Q^1$ together particularly preferably represent $C_3$-$C_4$-alkanediyl which is optionally mono- or disubstituted by methyl, ethyl, methoxy or ethoxy,
$Q^1$ particularly preferably represents hydrogen, $C_1$-$C_4$-alkyl, $C_1$-$C_4$-alkoxy-$C_1$-$C_2$-alkyl, or optionally methyl- or methoxy-substituted $C_3$-$C_6$-cycloalkyl, in which optionally one methylene group is replaced by oxygen, or phenyl or benzyl, each of which is optionally mono- or disubstituted by fluorine, chlorine, bromine, $C_1$-$C_4$-alkyl, $C_1$-$C_4$-alkoxy, trifluoromethyl or trifluoromethoxy, $Q^2$, $Q^3$, $Q^4$ independently of one another particularly preferably represent hydrogen, methyl or ethyl,
$Q^1$ and $Q^2$ together with the carbon to which they are attached particularly preferably represent optionally $C_1$-$C_4$-alkyl- or $C_1$-$C_4$-alkoxy-substituted saturated $C_5$-$C_6$-cycloalkyl in which optionally one ring member is replaced by oxygen, with the proviso that in this case A only represents hydrogen or $C_1$-$C_4$-alkyl,
G particularly preferably represents hydrogen (a) or represents one of the groups

 (b)

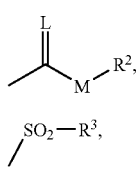 (c)

 (d)

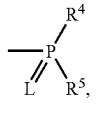 (e)

E or (f)

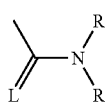 (g)

in particular (a), (b) or (c)

in which
E represents a metal ion or an ammonium ion,
L represents oxygen or sulphur and
M represents oxygen or sulphur,
$R^1$ particularly preferably represents $C_1$-$C_{16}$-alkyl, $C_2$-$C_{16}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to pentasubstituted by fluorine or chlorine, or $C_3$-$C_6$-cycloalkyl in which optionally one or two not directly adjacent ring members are replaced by oxygen and/or sulphur and which is optionally mono- or disubstituted by fluorine, chlorine, $C_1$-$C_4$-alkyl or $C_1$-$C_5$-alkoxy,
particularly preferably represents phenyl which is optionally mono- or disubstituted by fluorine, chlorine, bromine, cyano, nitro, $C_1$-$C_4$-alkyl, $C_1$-$C_4$-alkoxy, trifluoromethyl or trifluoromethoxy,
particularly preferably represents pyridyl or thienyl, each of which is optionally monosubstituted by fluorine, chlorine, bromine, methyl, ethyl or trifluoromethyl,
$R^2$ particularly preferably represents $C_1$-$C_{16}$-alkyl, $C_2$-$C_{16}$-alkenyl or $C_1$-$C_4$-alkoxy-$C_2$-$C_4$-alkyl,
particularly preferably represents $C_3$-$C_6$-cycloalkyl which is optionally mono- or disubstituted by methyl, ethyl or methoxy,
particularly preferably represents phenyl or benzyl, each of which is optionally mono- or disubstituted by fluorine, chlorine, bromine, cyano, nitro, $C_1$-$C_4$-alkyl, $C_1$-$C_4$-alkoxy, trifluoromethyl or trifluoromethoxy,
$R^3$ particularly preferably represents $C_1$-$C_4$-alkyl which is optionally mono- to pentasubstituted by fluorine or represents phenyl which is optionally mono- or disubstituted by fluorine, chlorine, bromine, $C_1$-$C_4$-alkyl, $C_1$-$C_4$-alkoxy, trifluoromethyl, trifluoromethoxy, cyano or nitro, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, or represents phenyl, benzyl, phenoxy or phenylthio, each of which is optionally mono- or disubstituted by fluorine, chlorine, bromine, nitro, cyano, $C_1$-$C_3$-alkoxy, trifluoromethyl, $C_1$-$C_3$-alkyl or trifluoromethyl, $R^5$ particularly preferably represents $C_1$-$C_4$-alkyl, $C_1$-$C_4$-alkoxy or $C_1$-$C_4$-alkylthio, $R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_6$-alkyl, represents phenyl which is optionally mono- or disubstituted by fluorine, chlorine, bromine, trifluoromethyl, $C_1$-$C_4$-alkyl or $C_1$-$C_4$-alkoxy, represents benzyl which is optionally substituted by fluorine, chlorine, bromine, methyl, ethyl, trifluoromethyl or methoxy, $R^7$ particularly preferably represents hydrogen, $C_1$-$C_6$-alkyl or $C_3$-$C_6$-alkenyl, $R^6$ and $R^7$ together, with nitrogen atom to which they are attached particularly preferably represent a $C_5$-$C_6$-alkylene radical in which optionally one methylene group is replaced by oxygen or sulphur and which is optionally mono- or disubstituted by methyl or ethyl.

In the radical definitions mentioned as being particularly preferred, halogen represents fluorine, chlorine and bromine, in particular fluorine and chlorine, especially fluorine, including as substituent, such as, for example, in halogenoalkyl.

Het very particularly preferably represents

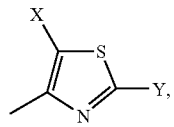

m very particularly preferably represents the number 0 or 1,

X very particularly preferably represents hydrogen, chlorine, bromine, methyl, ethyl, n-propyl or isopropyl, Y very particularly preferably represents the group

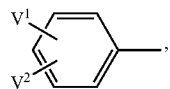

$V^1$ very particularly preferably represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy or 4-chlorophenoxy, $V^2$ very particularly preferably represents hydrogen, fluorine, chlorine, bromine, methyl, methoxy or trifluoromethyl, A very particularly preferably represents hydrogen, methyl, ethyl, n-propyl, isopropyl, n-butyl, isobutyl, tert-butyl, methoxymethyl, ethoxymethyl, phenyl or cyclohexyl, B very particularly preferably represents hydrogen, methyl or ethyl, A, B and the carbon atom to which they are attached very particularly preferably represent saturated $C_5$-$C_6$-cycloalkyl in which optionally one ring member is replaced by oxygen and which is optionally monosubstituted by methyl, ethyl, n-propyl, isopropyl, n-butyl, isobutyl, tert-butyl, trifluoromethyl, methoxy, ethoxy, n-propoxy, n-butoxy or isobutoxy, with the proviso that in this case $Q^1$ only represents hydrogen, A and $Q^1$ together very particularly preferably represent $C_3$-$C_4$-alkanediyl, $Q^1$ very particularly preferably represents hydrogen, methyl, ethyl, n-propyl, isopropyl, cyclopropyl, cyclopentyl, cyclohexyl or 4-chlorophenyl, $Q^2$, $Q^3$, $Q^4$ independently of one another very particularly preferably represent hydrogen, methyl or ethyl, $Q^1$ and $Q^2$ together with the carbon atom to which they are attached very particularly preferably represent optionally methyl-, ethyl-, methoxy-, ethoxy-, n-propoxy- or n-butoxy-substituted saturated $C_5$-$C_6$-cycloalkyl in which optionally one ring member is replaced by oxygen, with the proviso that in this case A only represents hydrogen, G very particularly preferably represents hydrogen (a) or represents one of the groups

(b)

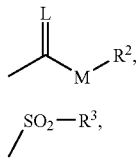

(c)

(d)

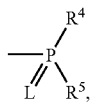

(e)

(f)

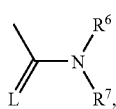

(g)

in particular (a), (b) or (c), in which

E represents a metal ion or an ammonium ion,

L represents oxygen or sulphur and

M represents oxygen or sulphur, $R^1$ very particularly preferably represents in each case optionally fluorine or chlorine-substituted $C_1$-$C_8$-alkyl, $C_2$-$C_8$-alkenyl, $C_1$-$C_2$-alkoxy-$C_1$-$C_2$-alkyl, $C_1$-$C_2$-alkylthio-$C_1$-$C_2$-alkyl or cyclopropyl or cyclohexyl, each of which is optionally monosubstituted by fluorine, chlorine, methyl, ethyl or methoxy, very particularly preferably represents phenyl which is optionally monosubstituted by fluorine, chlorine, bromine, cyano, nitro, methyl, ethyl, isopropyl, tert-butyl, methoxy, trifluoromethyl or trifluoromethoxy, very particularly preferably represents thienyl or pyridyl, each of which is optionally monosubstituted by fluorine, chlorine, bromine or methyl, $R^2$ very particularly preferably represents $C_1$-$C_8$-alkyl, $C_2$-$C_8$-alkenyl or $C_1$-$C_4$-alkoxy-$C_2$-alkyl, very particularly preferably represents $C_3$-$C_6$-cycloalkyl which is optionally monosubstituted by methyl, ethyl or methoxy, very particularly preferably represents phenyl or benzyl, each of which is optionally monosubstituted by fluorine, chlorine, cyano, nitro, methyl, ethyl, isopropyl, tert-butyl, methoxy, trifluoromethyl or trifluoromethoxy, $R^3$ very particularly preferably represents methyl or ethyl, each of which is optionally trisubstituted by fluorine or phenyl which is optionally monosubstituted by fluorine, chlorine, bromine, methyl, tert-butyl, methoxy, trifluoromethyl, trifluoromethoxy, cyano or nitro, $R^4$ very particularly preferably represents $C_1$-$C_4$-alkyl, $C_1$-$C_4$-alkoxy, $C_1$-$C_4$-alkylamino, di-($C_1$-$C_4$-alkyl)amino, $C_1$-$C_4$-alkylthio or represents phenyl, phenoxy or phenylthio, each of which is optionally monosubstituted by fluorine, chlorine, bromine, nitro, cyano, $C_1$-$C_2$-alkoxy, trifluoromethoxy or $C_1$-$C_3$-alkyl, $R^5$ very particularly preferably represents methyl, ethyl, methoxy, ethoxy, methylthio or ethylthio, $R^6$ very particularly preferably represents hydrogen, represents $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_1$-$C_4$-alkyl, $R^7$ very particularly preferably represents hydrogen, $C_1$-$C_4$-alkyl or $C_3$-$C_4$-alkenyl, $R^6$ and $R^7$ together with the nitrogen atom to which they are attached very particularly preferably represent a $C_5$-alkylene radical in which optionally one methylene group is replaced by oxygen.

Het most preferably represents

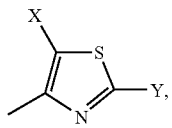

m most preferably represents the number 0 or 1,
X most preferably represents hydrogen, methyl or ethyl,
Y most preferably represents the group

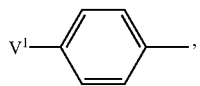

$V^1$ most preferably represents hydrogen, chlorine, methyl, ethyl, n-propyl, isopropyl, n-butyl, isobutyl, tert-butyl, trifluoromethyl or represents 4-chloro-phenoxy, A most preferably represents hydrogen, methyl, ethyl, n-propyl, isopropyl, n-butyl, isobutyl, phenyl or cyclohexyl, B most preferably represents hydrogen, methyl or ethyl, A, B and the carbon atom to which they are attached most preferably represent saturated $C_5$-$C_6$-cycloalkyl in which optionally one ring member is replaced by oxygen and which is optionally monosubstituted by methyl, ethyl, n-propyl, isopropyl, n-butyl, isobutyl, tert-butyl, methoxy, ethoxy, n-propoxy, n-butoxy or isobutoxy, with the proviso that in this case $Q^1$ only represents hydrogen, A and $Q^1$ together most preferably represent $C_3$-$C_4$-alkanediyl, $Q^1$ most preferably represents hydrogen, methyl, ethyl, n-propyl, isopropyl or 4-chlorophenyl, $Q^2$ most preferably represents hydrogen, methyl or ethyl, $Q^3$ most preferably represents hydrogen, $Q^4$ most preferably represents hydrogen, $Q^1$ and $Q^2$ together with the carbon atom to which they are attached most preferably represent saturated $C_5$-$C_6$-cycloalkyl, with the proviso that in this case A only represents hydrogen, G most preferably represents hydrogen (a) or represents one of the groups

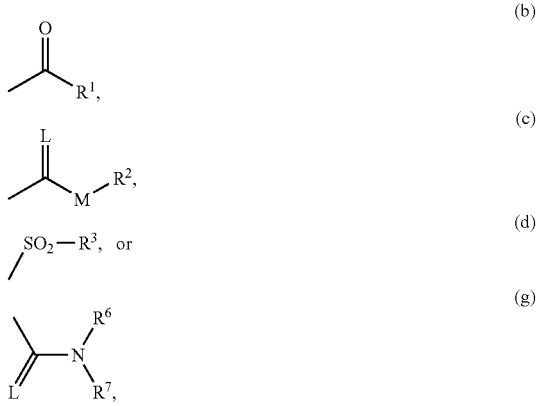

in which
L represents oxygen and
M represents oxygen or sulphur, $R^1$ most preferably represents $C_1$-$C_8$-alkyl, $C_1$-$C_2$-alkoxy-$C_1$-$C_2$-alkyl or cyclopropyl which is optionally monosubstituted by chlorine, represents phenyl which is optionally monosubstituted by chlorine, represents pyridyl which is optionally monosubstituted by chlorine, $R^2$ most preferably represents $C_1$-$C_8$-alkyl, represents phenyl or benzyl, $R^3$ most preferably represents methyl or ethyl, $R^6$ and $R^7$ together with the nitrogen atom to which they are attached most preferably represent a $C_5$-alkylene radical in which optionally one methylene group is replaced by oxygen.

The general or preferred radical definitions or illustrations given above can be combined with one another as desired, i.e. including combinations between the respective ranges and preferred ranges. They apply to the end products and, correspondingly, to precursors and intermediates.

Preference according to the invention is given to the compounds of the formula (I) which contain a combination of the meanings given above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Most preference according to the invention is given to the compounds of the formula (I) which contain a combination of the meanings given above as being most preferred.

Particular preference is given to compounds of the formula (I) in which G represents hydrogen.

Saturated or unsaturated hydrocarbon radicals, such as alkyl or alkenyl, can in each case be straight-chain or branched as far as this is possible, including in combination with heteroatoms, such as, for example, in alkoxy.

Unless indicated otherwise, optionally substituted radicals can be mono- or poly-substituted, where in the case of polysubstitution the substituents can be identical or different.

Using, for example, according to process (A) 1-[4-(5-methyl)-2-(4-chloro-phenyl)-thiazolyl]-3-(1-ethoxycarbonyl-cyclohexyl)-propanone as starting material, the course of the process according to the invention can be represented by the reaction scheme below:

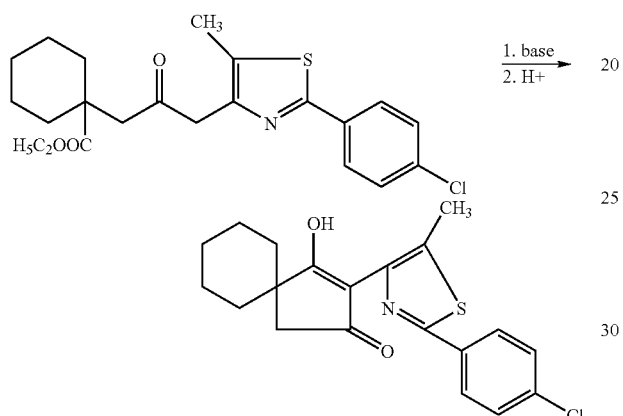

Using, for example, according to process (B) 1-[4-(5-methyl)-2-(4-chloro-phenyl)-thiazolyl]-4-(l-ethoxycarbonyl-cyclohexyl)-butan-2-one as starting material, the course of the process according to the invention can be represented by the following reaction scheme:

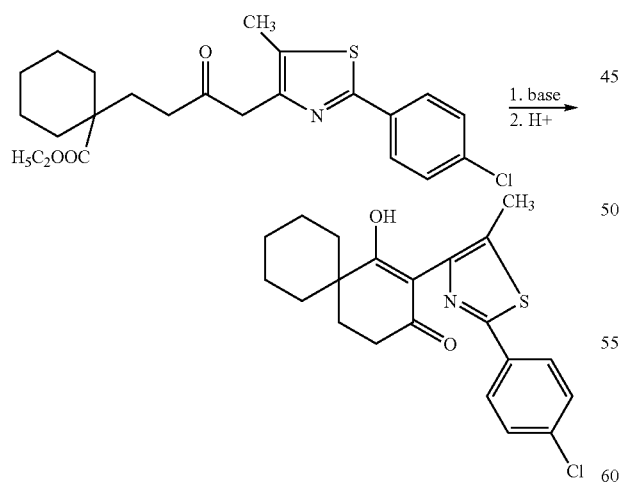

Using, for example, according to process (Dα) 2-[4-(5-methyl-2-(3-chloro-phenyl)-thiazolyl]-5,5-dimethylcyclohexane-1,3-dione and pivaloyl chloride as starting materials, the course of the process according to the invention can be represented by the following reaction scheme:

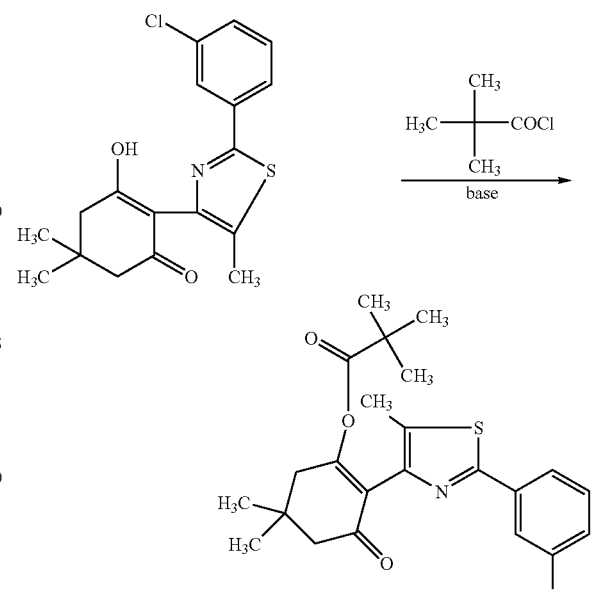

Using, for example, according to process (Dβ) 2-[4-(5-ethyl-2-(4-methoxy-phenyl))-thiazolyl]-5,5-dimethyl-cyclohexane-1,3-dione and acetic anhydride as starting materials, the course of the process according to the invention can be represented by the reaction scheme below:

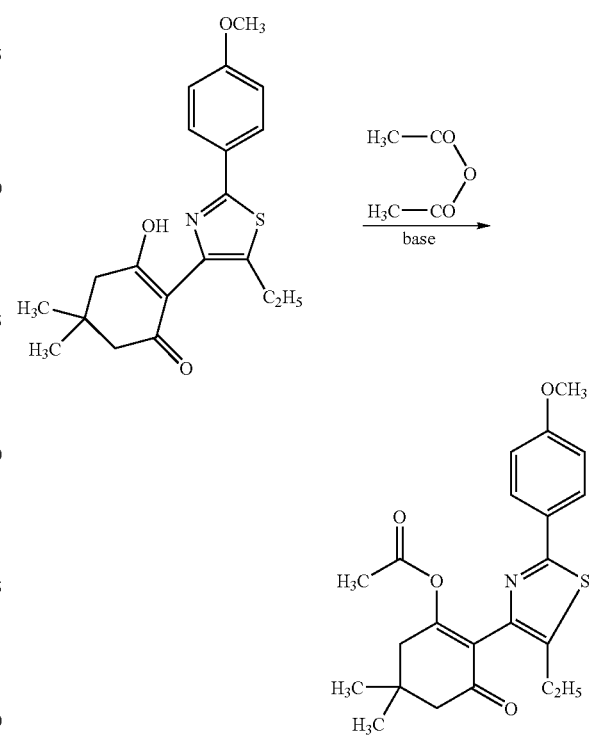

Using, for example, according to process (E) 2-[4-(5-methyl-2-phenyl)-thiazolyl]-5,5-dimethyl-cyclohexane-1,3-dione and ethoxyethyl chloroformate as starting materials, the course of the process according to the invention can be represented by the reaction scheme below:

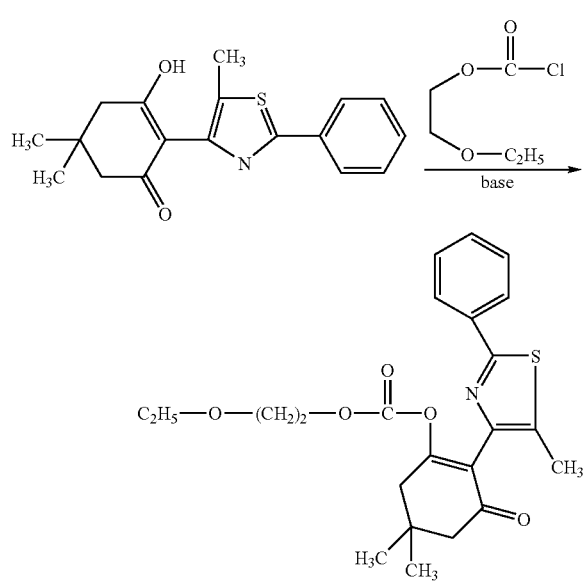

Using, for example, according to process (F), 2-[4-(5-methyl-2-(4-fluorophenyl))-thiazolyl]-4,4-dimethyl-cyclopentane-1,3-dione and methyl chloromonothioformate as starting materials, the course of the reaction can be represented as shown below:

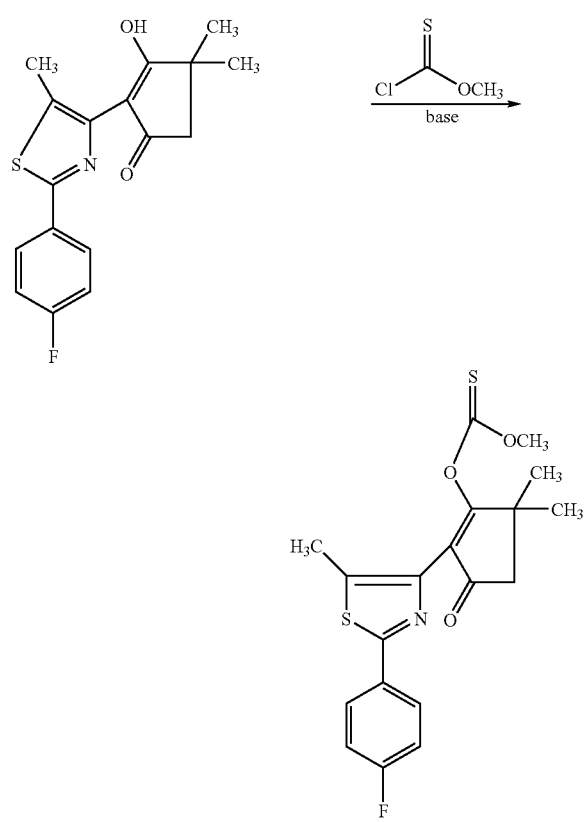

Using, for example, according to process (G) 2-[4-(5-methyl-3-(4-methyl-phenyl)-thiazolyl]-5,5-dimethyl-cyclohexane-1,3-dione and methanesulphonyl chloride as starting materials, the course of the reaction can be represented by the reaction scheme below:

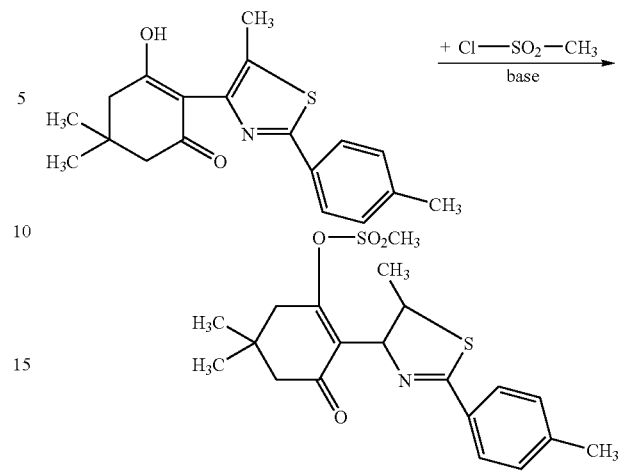

Using, for example, according to process (H) 2-[4-(5-methyl-2-phenyl)-thiazolyl]-4,4-dimethyl-cyclopentane-1,3-dione and 2,2,2-trifluoroethyl methanethio-phosphonyl chloride as starting materials, the course of the reaction can be represented by the reaction scheme below:

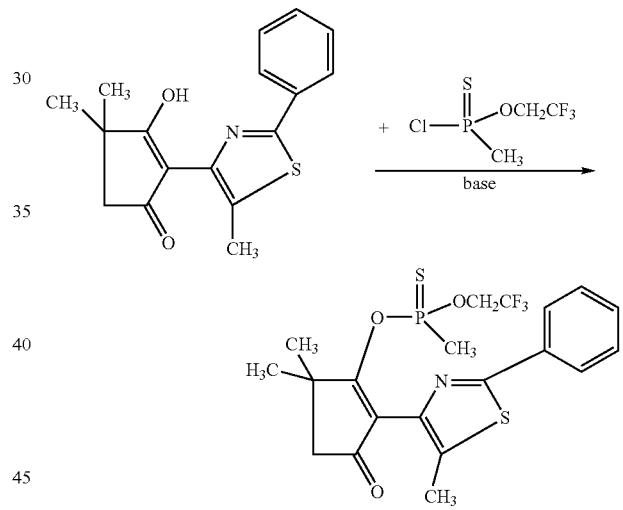

Using, for example, according to process (I) 2-[4-(5-methyl-2-(4-trifluornethyl-phenyl))-thiazolyl]-5,5-dimethyl-cyclohexane-1,3-dione and NaOH as components, the course of the process according to the invention can be represented by the reaction scheme below:

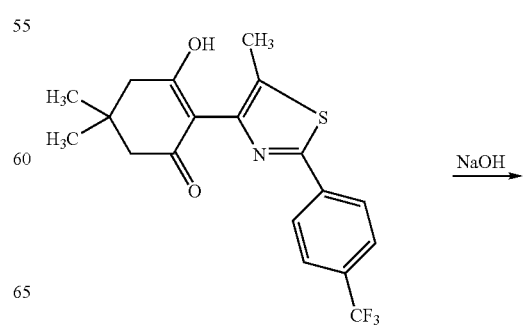

-continued

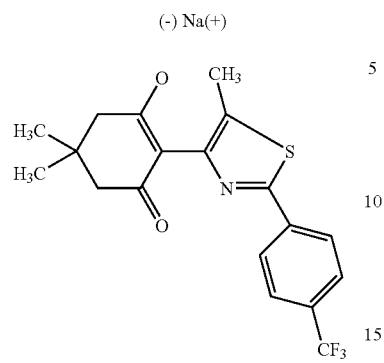

Using, for example, according to process (Jα) 2-[4-(5-methyl-2-(3-trifluoromethyl-phenyl))-thiazolyl]-4,4-dimethyl-cyclohexane-1,3-dione and ethyl isocyanate as starting materials, the course of the reaction can be represented by the reaction scheme below:

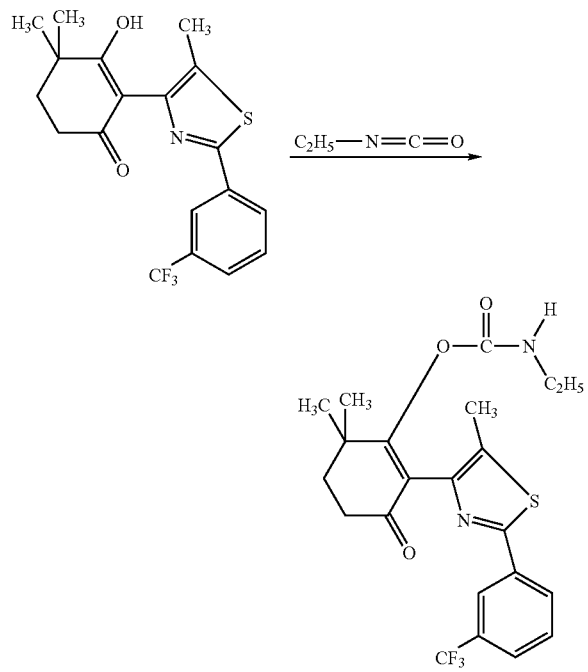

Using, for example, according to process (Jβ) 2-[4-(5-methyl-2-phenyl)-thiazolyl]-5,5-dimethyl-cyclohexyl-1,3-dione and dimethylcarbamoyl chloride as starting materials, the course of the reaction can be represented by the scheme below:

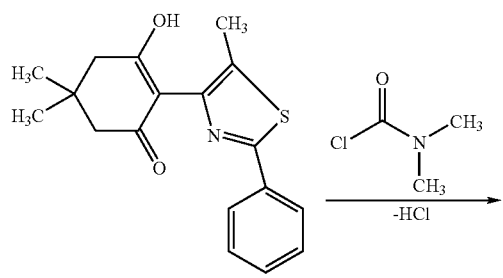

-continued

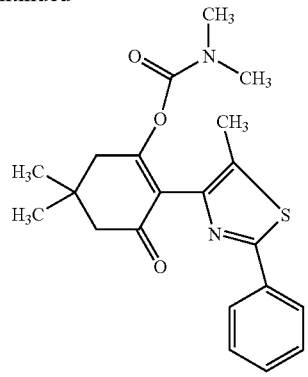

The ketocarboxylic esters of the formula (II)

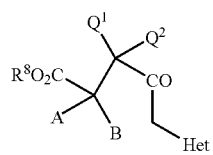

(II)

in which
A, B, Het, $Q^1$, $Q^2$ and $R^8$ are as defined above, which are required as starting materials in the above process (A), are novel.

They can be prepared by methods known in principle.

The 5-hetaryl-4-ketocarboxylic esters of the formula (II) are obtained, for example, when 5-hetaryl-4-ketocarboxylic acids of the formula (XIV)

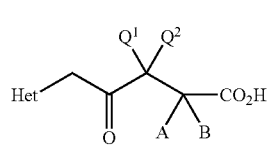

(XIV)

in which
A, B, Het, $Q^1$ and $Q^2$ are as defined above, are esterified (cf., for example, Organikum, 15th edition, Berlin, 1977, page 499) or alkylated (see Preparation Example).

The 5-hetaryl4-ketocarboxylic acids of the formula (XIV)

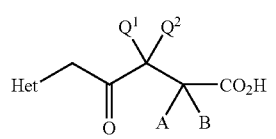

(XIV)

in which
A, B, Het, $Q^1$ and $Q^2$ are as defined above, are novel; they can however be prepared by methods known in principle (see Preparation Example).

The 5-hetaryl4-ketocarboxylic acids of the formula (XIV) are obtained, for example, when 2-hetaryl-3-oxo-adipic esters of the formula (XV)

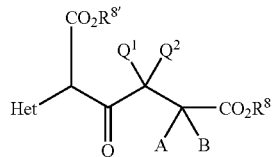
(XV)

in which
A, B, Het, $Q^1$ and $Q^2$ are as defined above and
R8 and $R^{8\prime}$ represent alkyl (in particular $C_1$-$C_8$-alkyl)

are decarboxylated, if appropriate in the presence of a diluent and if appropriate in the presence of a base or an acid (cf., for example Organikum, 15th edition, Berlin, 1977, pages 519-521).

The compounds of the formula (XV)

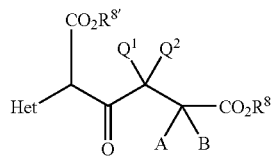
(XV)

in which
A, B, Het, $Q^1$, $Q^2$, $R^8$ and $R^{8\prime}$ are as defined above,
or, if the compound of the formula (XVII) was used as starting material for the preparation, in which case $R^8$ represents hydrogen, are novel.

The compounds of the formula (XV) are obtained, for example,
when dicarboxylic monoester chlorides of the formula (XVI),

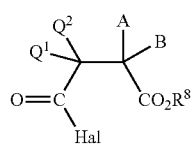
(XVI)

in which
A, B, $Q^1$, $Q^2$ and $R^8$ are as defined above and
Hal represents chlorine or bromine, or carboxylic anhydrides of the formula (XVII)

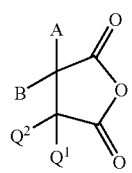
(XVII)

in which
A, B, $Q^1$ and $Q^2$ are as defined above, are acylated with a hetarylacetic ester of the formula (XVIII)

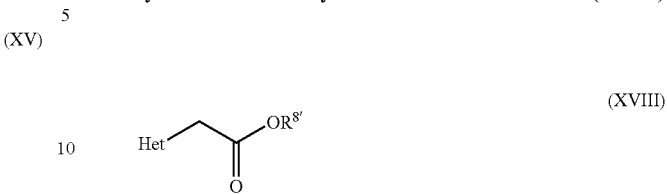
(XVIII)

in which
Het and $R^{8\prime}$ are as defined above, in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

Some of the compounds of the formulae (XVI) and (XVII) are known compounds of organic chemistry, and/or they can be prepared in a simple manner by methods known in principle.

The ketocarboxylic esters of the formula (III)

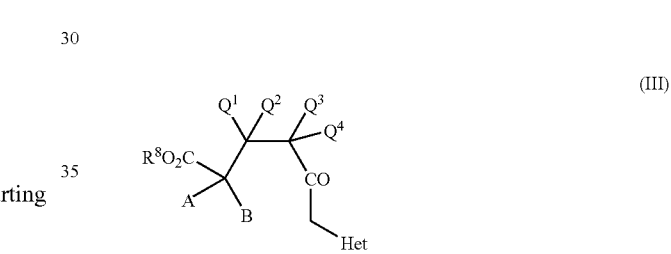
(III)

in which
A, B, Het, $Q^1$, $Q^2$, $Q^3$, $Q^4$ and $R^8$ are as defined above, which are required as starting materials for the above process (B), are novel.

They can be prepared by methods known in principle.

The 6-hetaryl-5-ketocarboxylic esters of the formula (III) are obtained, for example, when 6-hetaryl-5-ketocarboxylic acids of the formula (XIX)

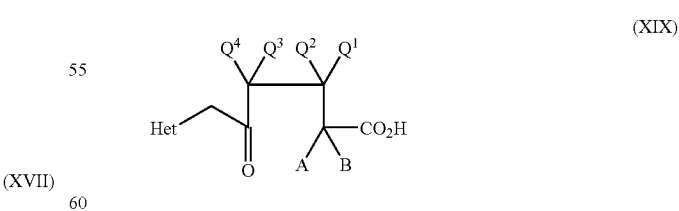
(XIX)

in which
A, B, Het, $Q^1$, $Q^2$, $Q^3$ and $Q^4$ are as defined above, are esterified (cf., for example, Organikum, 15th edition, Berlin, 1977, page 499) or alkylated (see Preparation Example).

The 6-aryl-5-ketocarboxylic acids of the formula (XIX)

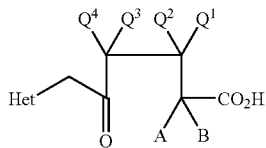
(XIX)

in which
A, B, Het, $Q^1$, $Q^2$, $Q^3$ and $Q^4$ are as defined above are novel. They can be prepared by methods known in principle, for example by hydrolysing and decarboxylating substituted 2-hetaryl-3-oxo-heptanedioic esters of the formula (XX)

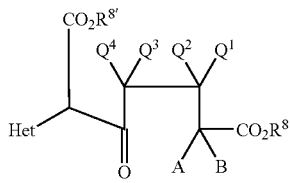
(XX)

in which
A, B, Het, $Q^1$, $Q^2$, $Q^3$ and $Q^4$ are as defined above and $R^8$ and $R^{8'}$ represent alkyl (preferably $C_1$-$C_6$-alkyl), if appropriate in the presence of a diluent and if appropriate in the presence of a base or an acid (cf., for example, Organikum, 15th edition, Berlin, 1977, pages 519-521).

The compounds of the formula (XX)

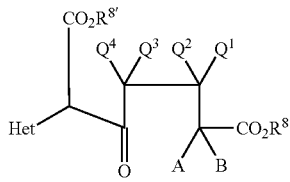
(XX)

in which
A, B, Het, $Q^1$, $Q^2$, $Q^3$, $Q^4$, $R^8$ and $R^{8'}$ are as defined above, or, if the compound of the formula (XXII) was used as starting material for the preparation, in which case $R^8$ represents hydrogen, are novel.

The compounds of the formula (XX) are obtained, for example, when dicarboxylic esters of the formula (XXI), or dicarboxylic anhydrides of the formula (XXII)

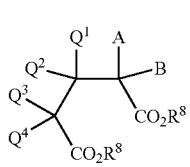
(XXI)

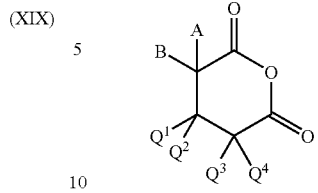
(XXII)

in which
A, B, $Q^1$, $Q^2$, $Q^3$, $Q^4$ and $R^8$ are as defined above, are condensed with a substituted hetarly acetic ester of the formula (XVII)

(XVIII)

in which
Het and $R^{8'}$ are as defined above, in the presence of a diluent and in the presence of a base.

Some of the compounds of the formulae (XXI) and (XXII) are commercially available, some are known, and/or they can be prepared by known processes.

Some of the compounds of the formula (XVIII) are novel; however, they can be prepared by processes known in principle:

1. C. S. Rooney et al. J. Med. Chem. 1983, 26, 700-714.
2. M. S. Malamas et al. J. Med. Chem. 1996, 39, 237-245.
3. J. L. Collins et al. J. Med. Chem. 1998, 41, 5037-5054.
4. EP-A-0 177 353.
5. EP-A-0 368 592.
6. NL-A-6614130.

The acyl halides of the formula (VI), carboxylic anhydrides of the formula (V), chloroformic esters or chloroformic thioesters of the formula (VI), chloromonothio-formic esters or chlorodithioformic esters of the formula (V), sulphonyl chlorides of the formula (VIII), phosphorus compounds of the formula (IX) and metal hydroxides, metal alkoxides or amines of the formulae (X) and (XI) and isocyanates of the formula (XII) and carbamoyl chlorides or thiocarbamoyl chlorides of the formula (XIII) furthermore required as starting materials for carrying out the processes (C), (D), (E), (F), (G), (H), and (I) according to the invention are generally known compounds of organic or inorganic chemistry.

Some of the compounds of the formulae (XVI), (XVII) and (XXI) are commercially available, some are known, and/or they can be prepared by methods known in principle.

The process (A) is characterized in that compounds of the formula (II) in which A, B, $Q^1$, $Q^2$, Het and $R^8$ are as defined above are subjected to an intramolecular condensation in the presence of a base.

Suitable for use as diluents in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methyl-pyrrolidone, and also alcohols, such as methanol, ethanol, propanol, iso-propanol, butanol, iso-butanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylamrnmonium bromide, Adogen 464 (=methyltrialkyl($C_8$-$C_{10}$)ammonium chloride) or TDA 1 (=tris-(methoxyethoxyethyl)-amine). It is furthermore possible to use alkali metals such as sodium or potassium. Furthermore, it is possible to use alkali metal and alkaline earth metal amides and hydrides, such as sodium amide, sodium hydride and calcium hydride, and, moreover, also alkali metal alkoxides, such as sodium methoxide, sodium ethoxide and potassium tert-butoxide.

When carrying out the process (A) according to the invention, the reaction temperatures can be varied within a relatively wide range. In general, the process is carried out at temperatures between −80° C. and 180° C., preferably between −50° C. and 120° C.

The process (A) according to the invention is generally carried out under atmospheric pressure.

When carrying out the process (A) according to the invention, the reaction components of the formula (II) and the deprotonating bases are generally employed in approximately double-equimolar amounts. However, it is also possible to use a relatively large excess (up to 3 mol) of one or the other component.

The process (B) is characterized in that compounds of the formula (III) in which A, B, $Q^1$, $Q^2$, $Q^3$, $Q^4$, Het and $R^8$ are as defined above are subjected to an intramolecular condensation in the presence of a diluent and in the presence of a base.

Suitable for use as diluents in the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. It is furthermore possible to use alcohols, such as methanol, ethanol, propanol, iso-propanol, butanol, iso-butanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)-amine). It is furthermore possible to use alkali metals such as sodium or potassium. Furthermore, it is possible to use alkali metal and alkaline earth metal amides and hydrides, such as sodium amide, sodium hydride and calcium hydride, and, moreover, also alkali metal alkoxides, such as sodium methoxide, sodium ethoxide and potassium tert-butoxide.

When carrying out the process (B) according to the invention, the reaction temperatures can be varied within a relatively wide range. In general, the process is carried out at temperatures between −80° C. and 180° C., preferably between −50° C. and 120° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one or the other component.

The process (C-α) is characterized in that compounds of the formulae (I-1-a) to (I-2-a) are in each case reacted with carbonyl halides of the formula (IV), if appropriate in the presence of a diluent and if appropriate in the presence of an acid binder.

Suitable diluents for the process (C-α) according to the invention are all solvents which are inert to the acyl halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, nitriles, such as acetonitrile, and also strongly polar solvents, such as dimethylformamide, dimethylacetamide, dimethyl sulphoxide and sulpholane. The hydrolytic stability of the acyl halide permitting, the reaction can also be carried out in the presence of water.

Suitable acid binders for the reaction according to the process (C-α) according to the invention are all customary acid acceptors. Preference is given to using tertiary amines, such as triethylamine, pyridine, diazabicyclooctane (DABCO), diazabi-cycloundecene (DBU), diazabicyclononene (DBN), Hünig base or N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (C-α) according to the invention can be varied within a relatively wide range. In general, the process is carried out at temperatures between −20° C. and +150° C., preferably between 0° C. and 100° C.

When carrying out the process (C-α) according to the invention, the starting materials of the formulae (I-1-a) to (I-2-a) and the carbonyl halide of the formula (IV) are generally each employed in approximately equivalent amounts. However, it is also possible to use a relatively large excess (up to 5 mol) of the carbonyl halide. Work-up is carried out by customary methods.

The process (C-β) is characterized in that compounds of the formulae (I1-a) to (I2-a) are reacted with carboxylic anhydrides of the formula (V), if appropriate in the presence of a diluent and if appropriate in the presence of an acid binder.

Suitable diluents for use in the process (C-β) according to the invention are preferably those solvents which are also preferred when acyl halides are used. Furthermore, it is also possible for a carboxylic anhydride employed in excess to act simultaneously as diluent.

Suitable acid binders, which are, if appropriate, added in the process (C-β), are preferably those acid binders which are also preferred when acyl halides are used.

The reaction temperatures in the process (C-β) according to the invention can be varied within a relatively wide range. In general, the process is carried out at temperatures between −20° C. and +150° C., preferably between 0° C. and 100° C.

When carrying out the process (C-β) according to the invention, the starting materials of the formulae (I-1-a) to (I2-a) and the carboxylic anhydride of the formula (V) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid that is formed are removed by distillation or by washing with an organic solvent or with water.

The process (D) is characterized in that compounds of the formulae (I1-a) to (I2-a) are in each case reacted with chlorofornic esters or chloroformic thiolesters of the formula (VI), if appropriate in the presence of a diluent and if appropriate in the presence of an acid binder.

Suitable acid binders for the reaction according to process (D) according to the invention are all customary acid acceptors. Preference is given to using tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (D) according to the invention are all solvents which are inert to the chloroformic esters or chloroformic thiolesters used. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, nitriles, such as acetonitrile, and also strongly polar solvents, such as dimethylformamide, dimethylacetamide, dimethyl sulphoxide and sulpholane.

When carrying out the process (D) according to the invention, the reaction temperatures can be varied within a relatively wide range. If the process is carried out in the presence of a diluent and an acid binder, the reaction temperatures are generally between $-20°$ C. and $+100°$ C., preferably between $0°$ C. and $50°$ C.

The process (D) according to the invention is generally carried out under atmospheric pressure.

When carrying out the process (D) according to the invention, the starting materials of the formulae (I-1-a) to (I2-a) and the appropriate chloroformic ester or chloroformic thiolester of the formula (VI) are generally each employed in approximately equivalent amounts. However, it is also possible to use a relatively large excess (up to 2 mol) of one or the other component. Work-up is carried out by customary methods. In general, precipitated salts are removed and the reaction mixture that remains is concentrated by stripping off the diluent.

Process (E) according to the invention is characterized in that compounds of the formulae (I1-a) to (I-2-a) are in each case reacted with compounds of the formula (VII), in the presence of a diluent and, if appropriate, in the presence of an acid binder.

In the preparation process (E), about 1 mol of chloromonothioformic ester or chlorodithioformic ester of the formula (VII) is employed per mole of starting material of the formulae (I-1-a) to (I2-a), at from 0 to $120°$ C., preferably at from 20 to $60°$ C.

Suitable diluents, which are added, if appropriate, are all inert polar organic solvents, such as nitrites, esters, ethers, amides, sulphones, sulphoxides, and also halogenoalkanes.

Preference is given to using acetonitrile, ethyl acetate, dimethyl sulphoxide, tetra-hydrofuran, dimethylformamide or methylene chloride.

If, in a preferred embodiment, the enolate salt of the compounds (I1-a) to (I-2-a) is prepared by adding strong deprotonating agents, such as, for example, sodium hydride or potassium tert-butoxide, the further addition of acid binders can be dispensed with.

If acid binders are used, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (F) according to the invention is characterized in that compounds of the formulae (I1-a) to (I2-a) are in each case reacted with sulphonyl chlorides of the formula (VIII), if appropriate in the presence of a diluent and if appropriate in the presence of an acid binder.

In the preparation process (F), about 1 mol of sulphonyl chloride of the formula. (VIII) is employed per mole of starting material of the formulae (I-1-a) to (I2-a), at from $-20$ to $150°$ C., preferably at from 20 to $70°$ C.

Suitable diluents which are added, if appropriate, are all inert polar organic solvents, such as nitrites, esters, ethers, amides, sulphones, sulphoxides, or halogenated hydrocarbons, such as methylene chloride.

Preference is given to using acetonitrile, ethyl acetate, dimethyl sulphoxide, tetra-hydrofuran, dimethylformamide, methylene chloride.

If, in a preferred embodiment, the enolate salt of the compounds (I1-a) to (I-2-a) is prepared by adding strong deprotonating agents (such as, for example, sodium hydride or potassium tert-butoxide), the further addition of acid binders can be dispensed with.

If acid binders are used, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (G) according to the invention is characterized in that compounds of the formulae (I1-a) to (I2-a) are in each case reacted with phosphorus compounds of the formula (IX), if appropriate in the presence of a diluent and if appropriate in the presence of an acid binder.

In the preparation process (G), to obtain compounds of the formulae (I-1-e) to (I-2-e), 1 to 2,preferably 1 to 1.3,mol of the phosphorus compound of the formula (IX) are employed per mole of the compounds (I1-a) to (I-2-a), at temperatures between $-40°$ C. and $150°$ C., preferably between $-10$ and $110°$ C.

Suitable diluents which are added, if appropriate, are all inert polar organic solvents, such as ethers, amides, nitrites, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added, if appropriate, are customary inorganic or organic bases, such as hydroxides, carbonates or amines. Examples which may be mentioned are sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods of organic chemistry. The end products obtained are preferably purified by crystallization, chromatographic purification or by "incipient distillation", i.e. removal of the volatile components under reduced pressure.

The process (H) is characterized in that compounds of the formulae (I-1-a) to (I2-a) are reacted with metal hydroxides or metal alkoxides of the formula (X) or amines of the formula (XI), if appropriate in the presence of a diluent.

Suitable for use as diluents in the process (H) according to the invention are, preferably, ethers, such as tetrahydrofuran, dioxane, diethyl ether, or else alcohols, such as methanol, ethanol, isopropanol, and also water.

The process (H) according to the invention is generally carried out under atmospheric pressure.

The reaction temperatures are generally between −20° C. and 100° C., preferably between 0° C. and 50° C.

The process (I) according to the invention is characterized in that compounds of the formulae (I-1-a) to (I2-a) are in each case reacted with compounds of the formula (XII) (I-α), if appropriate in the presence of a diluent and if appropriate in the presence of a catalyst, or (I-β) with compounds of the formula (XIII), if appropriate in the presence of a diluent and if appropriate in the presence of an acid binder.

In the preparation process (I-α), about 1 mol of isocyanate of the formula (XII) is employed per mole of starting material of the formulae (I1-a) to (I2-a), at from 0 to 100° C., preferably at from 20 to 50° C.

Suitable diluents which are added, if appropriate, are all inert organic solvents, such as ethers, amides, nitriles, sulphones, sulphoxides.

If appropriate, catalysts may be added to accelerate the reaction. Very advantageously, the catalysts which are employed are organotin compounds, such as, for example, dibutyltin dilaurate. The reaction is preferably carried out at atmospheric pressure.

In preparation process (I-β), about 1 mol of carbamoyl chloride of the formula (XIII) is reacted per mole of starting material of the formulae (I-1-a) to (I-2-a) at from −20 to 150° C., preferably at from 0 to 70° C.

Suitable diluents which are added, if appropriate, are all inert polar organic solvents, such as nitrites, esters, ethers, amides, sulphones, sulphoxides or halogenated hydrocarbons.

Preference is given to using acetonitrile, ethyl acetate, dimethyl sulphoxide, tetrahydrofuran, dimethylformamide or methylene chloride.

If, in a preferred embodiment, the enolate salt of the compounds (I-1-a) to (I2-a) is prepared by adding strong deprotonating agents (such as, for example, sodium hydride or potassium tert-butoxide), the addition of further acid binders can be dispensed with.

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dennestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Omithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus spp.*

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carbox),methylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be employed formulations in their as such or as a mixture with known fungicides, bactericides, acaricides, nematicides or insecticides in order to increase the activity spectrum or avoid the development of resistance. In many cases synergistic effects are achieved, ie. the efficacy of the mixture is greater than the efficacy of the individual components.

Favourable examples of co-components in mixtures are the following compounds:

Fungicides:

aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanoi, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxyrmid, tolclofos-methyl, tolyfluanid, triadimefon, triadimenol, triazbutil, triazoxide, trichlamide, tricyclazole, tridemorph, trifloxystrobin, triflurnizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl4'-trifluoromethoxy4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden4yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl4-[(3-methylbenzoyl)-oxy]-2,5-thiophenedicarboxylate, cis-1-(4-chlorophenyl)-2-(1H-1,2,4-triazol-1-yl)-cycloheptanol, cis4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
4-[(3,4-dimethoxyphenyl)-3-(4-fluorophenyl)-acryloyl]-morpholine.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
Bacillus popilliae, Bacillus sphaericus, Bacillus subtilis, Bacillus thuringiensis, baculoviruses, Beauveria bassiana, Beauveria tenella, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos,- chlorfluazuron, chlormephos, chlorpyrifos, chlorpyrifos M, chlovaporthrin, chromafenozide, cis-resmethrin, cispertmethrin, clocythrin, cloethocarb, clofentezine, clothianidine, cyanophos, cyclopren, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, Entomopfthora spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, Metharhizium anisopliae, metharhizium flavoviride, methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
Paecilomyces fumosoroseus, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, spirodiclofen, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, Verticillium lecanii,
YI 5302,
zeta-cypermethrin, zolaprofos,
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate,
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
Bacillus thuringiensis strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5] dec-3-en4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]4,5-dihydro4-phenyl-1H-pyrazole-1-carboxamide, N-[(2-chloro-5-thiazolyl)methyl]-N'methyl-N"-nitro-guanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl-[2-(dipropylamino)-2-oxoethyl]-ethylphosphoramidothioate,
N-cyanomethyl-4-trifluoromethyl-nicotinamide,
3,5-dichloro-1-(3,3-dichloro-2-propenyloxy)-4-[3-(5-trifluoromethylpyridin-2-yloxy)-propoxy]-benzene.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as by a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are understood as meaning plants with novel properties ("traits") which are grown by conventional cultivation, by mutagenesis or by recombinant DNA techniques. These may be cultivars, biotypes or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected. The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from Bacillus thuringiensis (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis*, *Periplaneta americana*, *Blattela germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formnulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.* Bristletails, such as *Lepisma saccharina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such; in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved. Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture or an aliphatic polar organic chemical solvent or solvent mixture is replaced. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling. agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes.

The, ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., in particular fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper (I) oxide, triethyltin chloride, tri-n-butyl(2-phenyl4-chlorophenoxy)tin, tributyltin oxide, molybdenum disulphide, antimony oxide, polymeric butyl titanate, phenyl-(bispyridine)bismuth chloride, tri-n-butyltin fluoride, manganese ethylenebis-thiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butyl-carbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb; or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleiimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, Oniscus asellus, Porcellio scaber.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*. From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive, evaporation systems, moth papers, moth bags and moth gels, as granules or dusts, in baits for spreading or in bait stations.

The active compounds according to the invention can also be used as defoliants, desiccants, haulm killers and, especially, as weedkillers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous crops of the genera: *Allium, Ananas, Asparagus, Avena, Hordeum, Oryza, Panicum, Saccharum, Secale, Sorghum, Triticale, Triticum, Zea*.

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flumetsulam, flumiclorac (-pentyl), flumioxazin, flumipropyn, flumetsulam, flumeturon, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, —P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, tniallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example:

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (—P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The substances according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis*;
*Sphaerotheca* species, such as, for example, *Sphaerotheca fuliginea*;
*Podosphaera* species, such as, for example, *Podosphaera leucotricha*;
*Venturia* species, such as, for example, *Venturia inaequalis*;
*Pyrenophora* species, such as, for example, *Pyrenophora teres* or *P. graminea* (conidia form: *Drechslera*, syn: *Helminthosporium*);
*Cochliobolus* species, such as, for example, *Cochliobolus sativus* (conidia form: *Drechslera*, syn: *Helminthosporium*);
*Uromyces* species, such as, for example, *Uromyces appendiculatus*;
*Puccinia* species, such as, for example, *Puccinia recondita*;
*Sclerotinia* species, such as, for example, *Sclerotinia sclerotiorum*;
*Tilletia* species, such as, for example, *Tilletia caries*;
*Ustilago* species, such as, for example, *Ustilago nuda* or *Ustilago avenae*;
*Pellicularia* species, such as, for example, *Pellicularia sasakii*;
*Pyricularia* species, such as, for example, *Pyricularia oryzae*;
*Fusarium* species, such as, for example, *Fusarium culmorum*;
*Botrytis* species, such as, for example, *Botrytis cinerea*;
*Septoria* species, such as, for example, *Septoria nodorum*;
*Leptosphaeria* species, such as, for example, *Leptosphaeria nodorum*;
*Cercospora* species, such as, for example, *Cercospora canescens*;
*Alternaria* species, such as, for example, *Alternaria brassicae*; and *Pseudocercosporella* species, such as, for example, *Pseudocercosporella herpotrichoides*.

The active compounds according to the invention also have very good fortifying action in plants. Accordingly, they can be used for mobilizing the defences of the plant against attack by undesirable microorganisms.

In the present context, plant-fortifying (resistance-inducing) substances are to be understood as meaning those substances which are capable of stimulating the defence system of plants such that, when the treated plants are subsequently inoculated with undesirable microorganisms, they show substantial resistance against these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. If appropriate, they can also be used as intermediates and precursors for the synthesis of further active compounds.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:
aldimorph, ampropylfos, ampropylfos-potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-alumninium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione; irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumnizole, triforine, triticonazole,
uniconazole,
validamycin A, vinclozolin, viniconazole,
zarilarnide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole, 1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl)-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methaneamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-pheny]-2-methylpropyl]-2,6-dimethyl-morpholine-hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methaneimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl1,2,3-benzothiadiazole-7-carbothioate,
spiro[2H]-1-benzopyrane-2,1'(3'H)-isobenzofuran]-3'-one,
4-[(3,4-dimethoxyphenyl)-3-(4-fluorophenyl)-acryloyl]-morpholine.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermnethrin, clocythrin, cloethocarb, clofentezine, clothianidine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn,
eflusilanate, emamectin, empenthrin, endosulfan, *Entomophthora* spp., esfenvalerate, ethiofencarb, ethion, ethoprophos, etofenprox, etoxazole, etrimfos;
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride,* methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus,* parathion A, parathion M, permethrin, phenthoate, phorat, phosalone, phosmet, phosphamidon, phoxim, pirimicarb, pirimiphos A, pirimiphos M, profenofos, promecarb, propargite, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlonrinphos, tetradifon theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI5302 zeta-cypermethfin, zolaprofos (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate, N-cyanomethyl-4-trifluoromethyl-nicotinamide, 3,5-dichloro-1-(3,3-dichloro-2-propenyloxy)-4-[3-(5-trifluoromethylpyridine-2-yloxy)-propoxy]-benzene.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

The preparation and the use of the active compounds according to the invention is illustrated by the examples below.

PREPARATION EXAMPLES

Example I-1-a-1

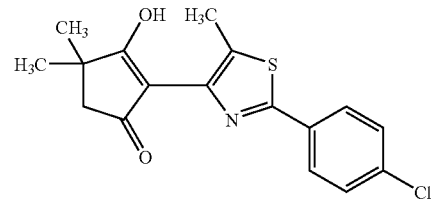

1.65 g (14.4 mmol) of potassium tert-butoxide are initially charged in 30 ml of anhydrous dimethylformamide (DMF), and 3.5 g (9.6 mmol) of the compound according to Example (II-1) in 10 ml of anhydrous DMF are added dropwise. The mixture is stirred at 50° C. for 3 h. 100 ml of ice-water are then poured into the reaction solution. This mixture is poured into 600 ml of cold 1N HCl solution. The precipitate is filtered off with suction and dried.

Yield: 2.9 g (90% of theory), m.p. 139-141° C.

The following compounds of the formula (I-1-a) were prepared analogously to Example (I-1-a-1) and in accordance with the general statements about the preparation:

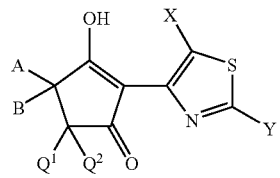

(I-1-a)

| Ex. No. | X | Y | B | A | Q¹ | Q² | m.p.° C. |
|---|---|---|---|---|---|---|---|
| I-1-a-2 | CH₃ | 4-Cl—C₆H₄ | —(CH₂)₅— | | H | H | 105-107° C. |
| I-1-a-3 | C₂H₅ | 4-Cl—C₆H₄ | —(CH₂)₅— | | H | H | 121-123° C. |
| I-1-a-4 | CH₃ | 4-Cl—C₆H₄ | —(CH₂)₂—O—(CH₂)₂— | | H | H | 130 |
| I-1-a-5 | CH₃ | 4-CF₃—C₆H₄ | —(CH₂)₅— | | H | H | Oil |
| I-1-a-6 | CH₃ | 4-Cl—C₆H₄ | H | —(CH₂)₄— | H | H | 145-148 |
| I-1-a-7 | CH₃ | 4-CH₃—C₆H₄ | —(CH₂)₅— | | H | H | 85 |
| I-1-a-8 | CH₃ | 4-Cl—C₆H₄—O—C₆H₄ | —(CH₂)₅— | | H | H | 75-77 |
| I-1-a-9 | CH₃ | 4-Cl—C₆H₄ | —(CH₂)₂—CHCH₃—(CH₂)₂— | | H | H | 142-144 |
| I-1-a-10 | CH₃ | 4-Cl—C₆H₄ | —(CH₂)₂—CHOCH₃—(CH₂)₂— | | H | H | 127 |
| I-1-a-11 | CH₃ | 4-Cl—C₆H₄ | H | C₆H₅— | H | H | 130 |
| I-1-a-12 | C₂H₅ | 4-Cl—C₆H₄ | —(CH₂)₂—O—(CH₂)₂— | | H | H | 210 |
| I-1-a-13 | CH₃ | 4-Cl—C₆H₄ | H | C₆H₁₁— | H | H | 105 |
| I-1-a-14 | CH₃ | 4-Cl—C₆H₄ | —(CH₂)₂—CH—C₃H₇—(CH₂)₂— | | H | H | oil |
| I-1-a-15 | CH₃ | 4-Cl—C₆H₄ | —(CH₂)₂—CH—t-C₄H₉—(CH₂)₂— | | H | H | oil |
| I-1-a-16 | CH₃ | 4-Cl—C₆H₄ | —(CH₂)₂—CH—C₂H₅—(CH₂)₂— | | H | H | oil |
| I-1-a-17 | H | 4-Cl—C₆H₄ | —(CH₂)₅— | | H | H | 185 |

Example I-1-b-1

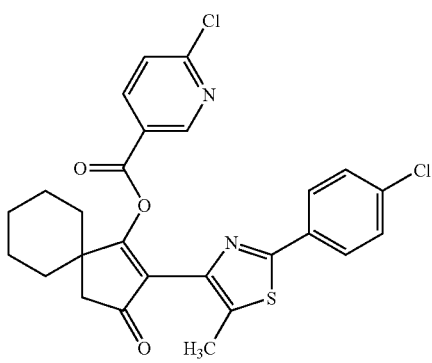

500 mg (1.33 mmol) of the compound according to Example I-1-a-2 are initially charged in 5 ml of absolute dichloromethane, and 0.27 ml (2.0 mmol) of triethylamine is added. At 0° C., 0.30 g (1.74 mmol) of 6-chloronicotinyl chloride is added, and the mixture is stirred at room temperature for 2 h. A further 0.15 g of chloronicotinyl chloride and 0.13 ml of triethylamine are then added.

The reaction mixture is washed with 10% citric acid solution, the aqueous phase is extracted with dichloromethane, and the organic phase is then washed with 1N aqueous sodium hydroxide solution and the aqueous phase is extracted with dichloromethane.

The organic phase is dried and the solvent is distilled off. The residue is stirred with petroleum ether and filtered and then dried.

Yield: 0.7 g (100% of theory), m.p. 133-134° C.

The following compounds of the formula (I-1-b) were obtained analogously to Example (I-1-b-1) and in accordance with the general statements about the preparation:

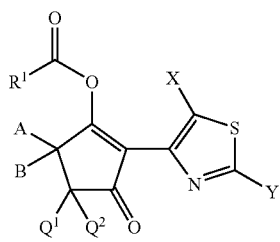

(I-1-b)

| Ex. No. | X | Y | B | A | Q¹ | Q² | R¹ | m.p.° C. |
|---|---|---|---|---|---|---|---|---|
| I-1-b-2 | CH₃ | 4-Cl—C₆H₄ | —(CH₂)₅— | | H | H | H₅C₂—O—CH₂— | 135 |
| I-1-b-3 | CH₃ | 4-Cl—C₆H₄ | —(CH₂)₅— | | H | H | i-C₃H₇ | oil |

-continued

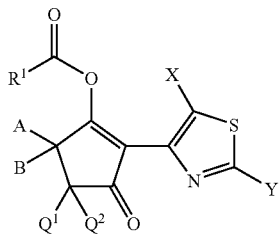
(I-1-b)

| Ex. No. | X | Y | B | A | Q¹ | Q² | R¹ | m.p.° C. |
|---|---|---|---|---|---|---|---|---|
| I-1-b-4 | $CH_3$ | 4-Cl—$C_6H_4$ | —$(CH_2)_5$— | H | H | | 4-Cl—$C_6H_4$ | 129-130 |
| I-1-b-5 | $CH_3$ | 4-Cl—$C_6H_4$ | —$(CH_2)_5$— | H | H | | (cyclopropyl-Cl) | Oil |

Example I-1-c-1

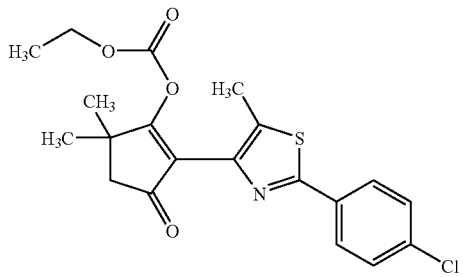

500 mg (1.5 mmol) of the compound according to Example (I-1-a-1) are initially charged in 5 ml of absolute dichloromethane, and 0.3 ml (2.25 mmol) of triethylamine is added. At 0° C., 0.225 g (1.95 mmol) of ethyl chloroformate is added, and the mixture is stirred at room temperature for 2 h.

The reaction solution is washed with 10% strength citric acid and the aqueous phase is extracted with dichloromethane ($CH_2Cl_2$). The organic phase is washed with 1N sodium hydroxide solution, dried and concentrated.

Yield: 0.45 g (75% of theory), 132-134° C.

The following compounds of the formula (I-1-c) were obtained analogously to Example (I-1-c-1) and in accordance with the general statements about the preparation:

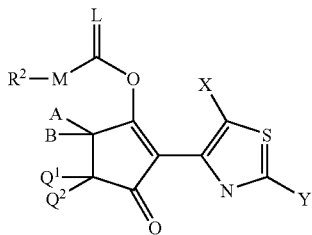
(I-1-c)

| Ex.No. | X | Y | A | B | Q¹ | Q² | L | M | R² | m.p.° C. |
|---|---|---|---|---|---|---|---|---|---|---|
| I-1-c-2 | $CH_3$ | 4-Cl—$C_6H_4$ | —$(CH_2)_5$— | | H | H | O | O | $C_2H_5$ | oil |
| I-1-c-3 | $C_2H_5$ | 4-Cl—$C_6H_4$ | —$(CH_2)_5$— | | H | H | O | O | $C_2H_5$ | oil |
| I-1-c-4 | $CH_3$ | 4-Cl—$C_6H_4$ | —$(CH_2)_5$— | | H | H | O | O | $C_6H_5$ | 139-140 |
| I-1-c-5 | $CH_3$ | 4-Cl—$C_6H_4$ | —$(CH_2)_5$— | | H | H | O | S | $C_6H_5$—$CH_2$ | 144 |
| I-1-c-6 | $CH_3$ | 4-Cl—$C_6H_4$ | —$(CH_2)_5$— | | H | H | O | O | $C_6H_5$—$CH_2$ | 137 |

Example I-1-d-1

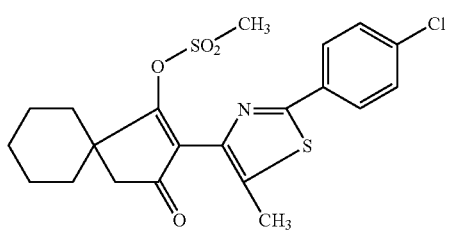

0.5 g (1.33 mmol) of the compound according to Example I-1-a-2 is initially charged in 5 ml of anhydrous dichloromethane, and 0.27 ml (2.0 mmol) of triethylamine is added. With ice-cooling, 0.135 ml (1.74 mmol) of methanesulphonyl chloride is added. The mixture is stirred at room temperature for 2 h.

The reaction mixture is extracted with 10% strength citric acid, the aqueous phase is washed with dichloromethane, the organic phase is extracted with 1N sodium hydroxide solution and the aqueous phase is washed with dichloromethane, dried and concentrated.

Yield: 0.6 g (100% of theory), m.p. 134° C.

$^1$H-NMR (d$_6$-DMSO, 400 MHz): δ=1.02-1.75 (m, 10H, cyc-hexyl-CH$_2$), 2.30 (s, 3H, thiazolyl-CH$_3$), 3.05 (s, 2H, CH$_2$—CO), 3.61 (s, 3H, SO$_2$—CH$_3$), 7.54 (d, 2H, Ar-H), 7.86 (d, 2H, Ar-H) ppm.

Example I-1-g-1

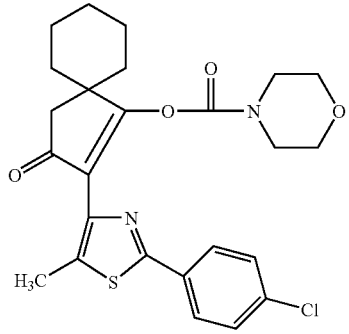

0.5 g (1.33 mmol) of the compound according to Example I-1-a-2 and 0.27 ml (2.0 mmol) of triethylamine are dissolved in 5 ml of anhydrous dichloromethane, and 0.26 g (1.73 mmol) of morpholine N-carbonyl chloride are added with ice-cooling. The mixture is stirred at room temperature overnight.

The reaction mixture is extracted with 10% strength citric acid, the aqueous phase is washed with dichloromethane, the organic phase is extracted with 1N sodium hydroxide solution and the aqueous phase is washed with dichloromethane, dried and concentrated.

Yield: 0.69 g (93% of theory), wax $^1$H-NMR (d$_6$-DMSO, 400 MHz): δ=1.02-1.74 (m, 10H, cyc-hexyl-CH$_2$), 2.30 (s, 3H, thiazolyl-CH$_3$), 3.01 (s, 2H, CH$_2$—CO), 3.05-3.79 (m, 8H, morpholine-CH$_2$), 7.54 (d, 2H, Ar-H), 7.85 (d, 2H, Ar-H) ppm.

Example II-1

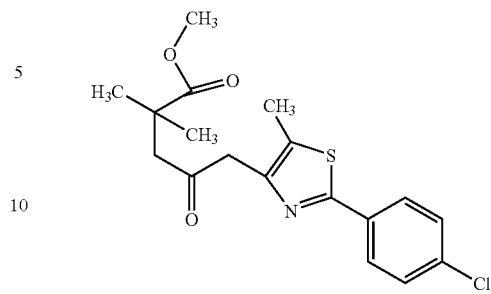

17.3 g (30 mmol) of the compound according to Example XIV-1 are initially charged in 200 ml of anhydrous acetone, and 6.8 g (49 mmol) of potassium carbonate and 20.5 g (147 mmol) of methyl iodide are added. The mixture is stirred under reflux for 16 h.

The solution is filtered, the solvent is distilled off and the residue is purified by silica gel chromatography (dichloromethane:petroleum ether, 4:1→dichloromethane→dichloromethane:ethyl acetate, 30:1→10:1).

Yield: 3.5 g (31% of theory), oil $^1$H-NMR (d$_6$-DMSO, 400 MHz): δ=1.11 (s, 6H, 2-CH$_3$—C-aliph.), 2.31 (s, 3H, CH$_3$—C-heteroarom.) 3.50 (s, 3H, CH$_3$—O), 7.50 (d, 2H, 2-CH-arom.), 7.84 (d, 2H, 2-CH-arom) ppm.

Example XIV-1

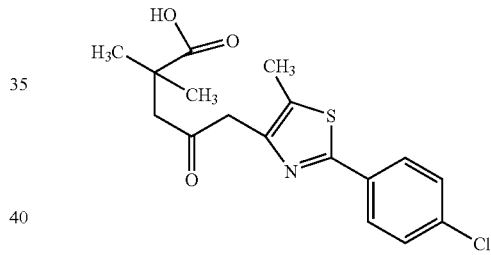

A solution of 12.7 g (45 mmol) of methyl 4-[2-(4-chlorophenyl)-5-methyl]-thiazolyl-acetate in 15 ml of tetrahydrofuran is, at −15° C., added dropwise to a solution of 25 ml of LDA* solution (2 molar) in 50 ml of anhydrous tetrahydrofuran, and the mixture is stirred at 0° C. for 60 min.

LDA=lithium diisopropylamide

At −15° C., a solution of 3.8 g (30 mmol) of 2,2-dimethylsuccinic anhydride in 10 ml of anhydrous tetrahydrofuran is then added dropwise.

The solution is stirred at room temperature for two hours, 75 ml of water and 20 g of ammonium chloride are then added and the solution is acidified using concentrated hydrochloric acid.

The intermediate is extracted with ether and the solvent is distilled off. The residue is boiled under reflux with 25 g KOH and 170 ml of water for one day.

The mixture is cooled, acidified with conc. hydrochloric acid and extracted with ether. The crude product is directly, without further characterization and purification, converted into the compound II-1.

Yield: 17.5 g (100% of theory), oil

The following compounds of the formula (II) were obtained analogously to Example (II-1) and in accordance with the general statements about the preparation:

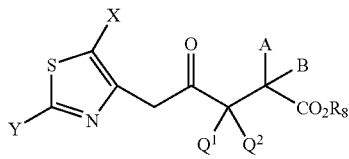

(II)

| Ex. No. | X | Y | B | A | $Q^1$ | $Q^2$ | $R^8$ | m.p.° C. |
|---|---|---|---|---|---|---|---|---|
| II-2 | $CH_3$ | 4-Cl—$C_6H_4$ | —$(CH_2)_5$— | | H | H | $CH_3$ | oil |
| II-3 | $C_2H_5$ | 4-Cl—$C_6H_4$ | —$(CH_2)_5$— | | H | H | $CH_3$ | oil |
| II-4 | $CH_3$ | 4-Cl—$C_6H_4$ | —$(CH_2)_2$—O—$(CH_2)_2$— | | H | H | $CH_3$ | oil |
| II-5 | $CH_3$ | 4-$CF_3$—$C_6H_4$ | —$(CH_2)_5$— | | H | H | $CH_3$ | oil |
| II-6 | $CH_3$ | 4-Cl—$C_6H_4$ | H | —$(CH_2)_4$— | H | H | $CH_3$ | oil |
| II-7 | $CH_3$ | 4-$CH_3$—$C_6H_4$ | —$(CH_2)_5$— | | H | H | $CH_3$ | oil |
| II-8 | $CH_3$ | 4-Cl—$C_6H_4$—O—$C_6H_4$ | —$(CH_2)_5$— | | H | H | $CH_3$ | oil |
| II-9 | $CH_3$ | 4-Cl—$C_6H_4$ | —$(CH_2)_2$—$CHCH_3$—$(CH_2)_2$— | | H | H | $CH_3$ | oil |
| II-10 | $CH_3$ | 4-Cl—$C_6H_4$ | —$(CH_2)_2$—$CHOCH_3$—$(CH_2)_2$— | | H | H | $CH_3$ | oil |
| II-11 | $CH_3$ | 4-Cl—$C_6H_4$ | H | $C_6H_5$— | H | H | $CH_3$ | oil |
| II-12 | $C_2H_5$ | 4-Cl—$C_6H_4$ | —$(CH_2)_2$—O—$(CH_2)_2$— | | H | H | $CH_3$ | oil |
| II-13 | $CH_3$ | 4-Cl—$C_6H_4$ | H | $C_6H_{11}$ | H | H | $CH_3$ | oil |
| II-14 | $CH_3$ | 4-Cl—$C_6H_4$ | —$(CH_2)_2$—CH—$C_3H_7$—$(CH_2)_2$— | | H | H | $CH_3$ | oil |
| II-15 | $CH_3$ | 4-Cl—$C_6H_4$ | —$(CH_2)_2$—CH—t-$C_4H_9$—$(CH_2)_2$— | | H | H | $CH_3$ | oil |
| II-16 | $CH_3$ | 4-Cl—$C_6H_4$ | —$(CH_2)_2$—CH—$C_2H_5$—$(CH_2)_2$— | | H | H | $CH_3$ | oil |
| II-17 | H | 4-Cl—$C_6H_4$ | —$(CH_2)_5$— | | H | H | $CH_3$ | oil |

The following compounds of the formula (XIV) were obtained analogously to Example (XIV-1) and in accordance with the general statements about the preparation:

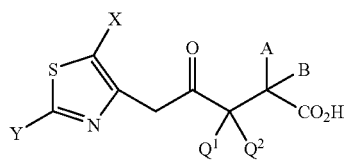

(XIV)

| Ex. No. | X | Y | B | A | $Q^1$ | $Q^2$ | m.p.° C. |
|---|---|---|---|---|---|---|---|
| XIV-2 | $CH_3$ | 4-Cl—$C_6H_4$ | —$(CH_2)_5$— | | H | H | wax |
| XIV-3 | $C_2H_5$ | 4-Cl—$C_6H_4$ | —$(CH_2)_5$— | | H | H | wax |
| XIV-4 | $CH_3$ | 4-Cl—$C_6H_4$ | —$(CH_2)_2$—O—$(CH_2)_2$— | | H | H | oil |
| XIV-5 | $CH_3$ | 4-$CF_3$—$C_6H_4$ | —$(CH_2)_5$— | | H | H | oil |
| XIV-6 | $CH_3$ | 4-Cl—$C_6H_4$ | H | —$(CH_2)_4$— | H | H | oil |
| XIV-7 | $CH_3$ | 4-$CH_3$—$C_6H_4$ | —$(CH_2)_5$— | | H | H | oil |
| XIV-8 | $CH_3$ | 4-Cl—$C_6H_4$—O—$C_6H_4$ | —$(CH_2)_5$— | | H | H | oil |
| XIV-9 | $CH_3$ | 4-Cl—$C_6H_4$ | —$(CH_2)_2$—$CHCH_3$—$(CH_2)_2$— | | H | H | oil |
| XIV-10 | $CH_3$ | 4-Cl—$C_6H_4$ | —$(CH_2)_2$—$CHOCH_3$—$(CH_2)_2$— | | H | H | oil |
| XIV-11 | $CH_3$ | 4-Cl—$C_6H_4$ | H | $C_6H_5$— | H | H | oil |
| XIV-12 | $C_2H_5$ | 4-Cl—$C_6H_4$ | —$(CH_2)_2$—O—$(CH_2)_2$— | | H | H | oil |
| XIV-13 | $CH_3$ | 4-Cl—$C_6H_4$ | H | $C_6H_{11}$— | H | H | oil |
| XIV-14 | $CH_3$ | 4-Cl—$C_6H_4$ | —$(CH_2)_2$—CH—$C_3H_7$—$(CH_2)_2$— | | H | H | oil |
| XIV-15 | $CH_3$ | 4-Cl—$C_6H_4$ | —$(CH_2)_2$—CH—t-$C_4H_9$—$(CH_2)_2$— | | H | H | oil |
| XIV-16 | $CH_3$ | 4-Cl—$C_6H_4$ | —$(CH_2)_2$—CH—$C_2H_5$—$(CH_2)_2$— | | H | H | oil |
| XIV-17 | H | 4-Cl—$C_6H_4$ | —$(CH_2)_5$— | | H | H | oil |

Example I-2-a-1

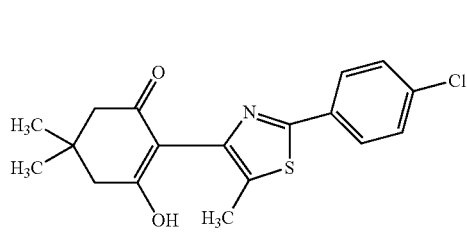

Example I-2-b-1

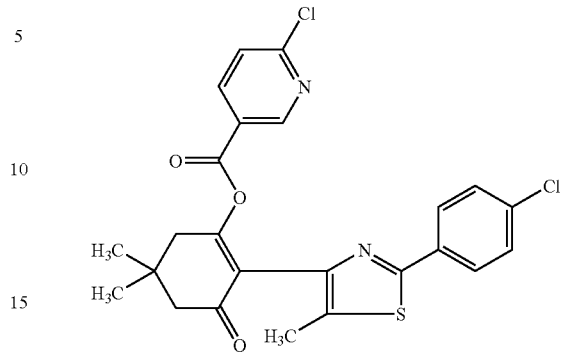

2.16 g (18.1 mmol) of potassium tert-butoxide are initially charged in 20 ml of anhydrous dimethylformamide, and 4.6 g (12.1 mmol) of the compound according to Example III-1 in 2 ml of anhydrous dimethylformamide are added dropwise.

The mixture is stirred at 50° C. for 2 hours.

The reaction solution is poured into 100 ml of ice-water, and this mixture is stirred into 500 ml of cold 1N hydrochloric acid solution. The precipitate is filtered off with suction and taken up in dichloromethane. The solvent is distilled off, and the residue is then purified by silica gel chromatography (cyclohexane/ethyl acetate, 5:1).

Yield: 1.4 g (13% of theory), m.p. 165-167° C.

The following compounds of the formula (I-2-a) were obtained analogously to Example (I-2-a-1) and in accordance with the general statements about the preparation:

500 mg (1.44 mmol) of the compound according to Example I-2-a-1 are initially charged in 5 ml of anhydrous dichloromethane, and 0.29 ml (2.16 mmol) of triethylamine is added. At 0° C., 0.33 g (1.87 mmol) of 6-chloronicotinyl chloride is added, and the mixture is stirred at room temperature for 2 h.

The reaction mixture is extracted with 10% citric acid, the aqueous phase is washed with dichloromethane, the organic phase is extracted with 1N sodium hydroxide solution and the aqueous phase is washed with dichloromethane, dried and concentrated.

Yield: 0.7 g (100% of theory), m.p. 127-130° C.

The following compounds of the formula (I-2-b) were obtained analogously to Example (I-2-b-1) and in accordance with the general statements about the preparation:

(I-2-a)

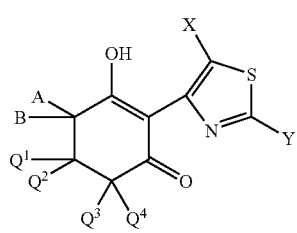

| Ex. No. | X | Y | A | B | Q¹ | Q² | Q³ | Q⁴ | m.p.° C. |
|---|---|---|---|---|---|---|---|---|---|
| I-2-a-2 | CH₃ | 4-Cl—C₆H₄ | H | H | H | H | H | H | 106 |
| I-2-a-3 | CH₃ | 4-Cl—C₆H₄ | CH₃ | CH₃ | H | H | H | H | oil |
| I-2-a-4 | CH₃ | 4-Cl—C₆H₄ | H | H | —(CH₂)₄— | | H | H | 122 |
| I-2-a-5 | CH₃ | 4-Cl—C₆H₄ | H | H | 4-Cl—C₆H₄ | H | H | H | 195-197 |

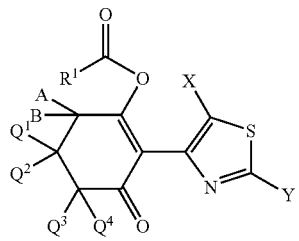

(I-2-b)

| Ex. No. | X | Y | A | B | Q¹ | Q² | Q³ | Q⁴ | R¹ | m.p.° C. |
|---|---|---|---|---|---|---|---|---|---|---|
| I-2-b-2 | $CH_3$ | $4\text{-}Cl\text{-}C_6H_4$ | H | H | $CH_3$ | $CH_3$ | H | H | $i\text{-}C_3H_7\text{-}$ | 96 |
| I-2-b-3 | $CH_3$ | $4\text{-}Cl\text{-}C_6H_4$ | H | H | $CH_3$ | $CH_3$ | H | H | $H_5C_2\text{-}O\text{-}CH_2\text{-}$ | 142 |
| I-2-b-4 | $CH_3$ | $4\text{-}Cl\text{-}C_6H_4$ | H | H | $CH_3$ | $CH_3$ | H | H | $4\text{-}Cl\text{-}C_6H_4$ | 123-125 |
| I-2-b-5 | $CH_3$ | $4\text{-}Cl\text{-}C_6H_4$ | H | H | $CH_3$ | $CH_3$ | H | H | (cyclopropyl-Cl) | 125 |

Example 1-2-c-1

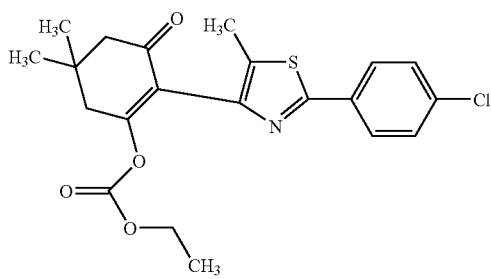

600 mg (1.7 mmol) of the compound according to Example I-2-a-1 are initially charged in 5 ml of anhydrous dichloromethane, and 0.35 ml (2.60 mmol) of triethylamine is added. At 0° C., 0.255 g (2.21 mmol) of ethyl chloroformate is added, and the mixture is stirred at room temperature for 2 hours.

The solution is washed with 10% strength citric acid and the aqueous phase is extracted with dichloromethane. The organic phase is washed with 1N sodium hydroxide solution, dried and concentrated.

Yield: 0.62 g (87% of theory), m.p. 82-86° C.

The following compounds of the formula (I-2-c) were obtained analogously to Example (I-2-c-1) and in accordance with the general statements about the preparation:

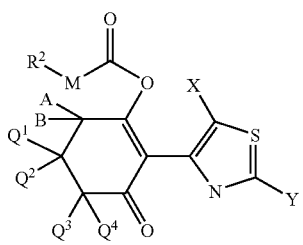

(I-2-c)

| Ex. No. | X | Y | A | B | Q¹ | Q² | Q³ | Q⁴ | M | R² | m.p.° C. |
|---|---|---|---|---|---|---|---|---|---|---|---|
| I-2-c-2 | $CH_3$ | $4\text{-}Cl\text{-}C_6H_4$ | H | H | $CH_3$ | $CH_3$ | H | H | O | $C_6H_5\text{-}$ | 123-125 |
| I-2-c-3 | $CH_3$ | $4\text{-}Cl\text{-}C_6H_4$ | H | H | $CH_3$ | $CH_3$ | H | H | O | $C_6H_5\text{-}CH_2$ | 129-131 |
| I-2-c-4 | $CH_3$ | $4\text{-}Cl\text{-}C_6H_4$ | H | H | $CH_3$ | $CH_3$ | H | H | S | $C_6H_5\text{-}CH_2$ | 94 |

Example No. I-2-d-1

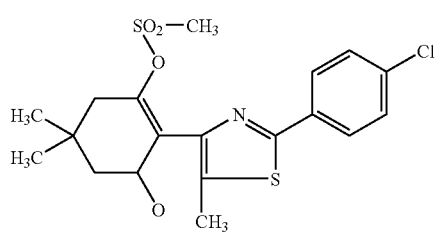

500 mg (1.44 mmol) of the compound according to Example I-2-a-1 are initially charged in 5 ml of anhydrous dichloromethane, and 0.29 ml (2.16 mmol) of triethylamine is added. At 0° C., 0.22 g (1.87 mmol) of methylsulphonyl chloride is added, and the mixture is stirred at room temperature for 2 h.

The reaction mixture is extracted with 10% strength citric acid, the aqueous phase is washed with dichloromethane, the organic phase is extracted with 1N NaOH and the aqueous phase is washed with dichloromethane, dried and concentrated.

Yield: 0.65 g (100% of theory), wax

1H-NMR ($d_6$-DMSO, 400 MHz):

δ=1.17 (s, 6H, cyc-hexyl-$CH_3$), 2.25 (s, 3H, thiazolyl-$CH_3$), 2.48 (s, 2H, cyc-hexyl-$CH_2$), 2.86 (s, 2H, cyc-hexyl-$CH_2$), 3.21 (s, 3H, $SO_2$—$CH_3$), 7.52 (d, 2H, Ar—H), 7.83 (d, 2H, Ar—H) ppm.

Example No. I-2-g-1

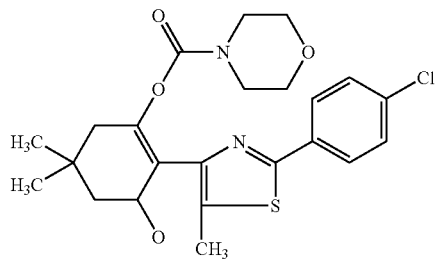

500 mg (1.44 mmol) of the compound according to Example I-2-a-1 are initially charged in 5 ml of anhydrous dichloromethane, and 0.29 ml (2.16 mmol) of triethylamine is added. At 0° C., 0.27 g (1.87 mmol) of morpholinecarbonyl chloride is added, and the mixture is stirred at room temperature for 2 h.

The reaction mixture is extracted with 10% strength citric acid, the aqueous phase is washed with dichloromethane, the organic phase is extracted with 1N sodium hydroxide solution and the aqueous phase is washed with dichloromethane, dried and concentrated.

Yield: 0.65 g (100% of theory), m.p. 128° C.

1H-NMR ($d_6$-DMSO, 400 MHz):

δ=1.13 (s, 6H, cyc-hexyl-$CH_3$), 2.21 (s, 3H, thiazolyl-$CH_3$), 2.46 (s, 2H, cyc-hexyl-$CH_2$), 2.71 (s, 2H, cyc-hexyl-$CH_2$), 3.06-3.80 (m, 8H, morpholine-$CH_2$), 7.53 (d, 2H, Ar—H), 7.84 (d, 2H, Ar—H) ppm.

Example III-1

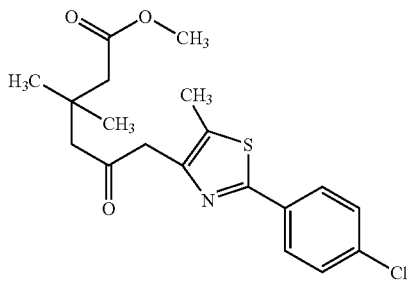

17.0 g (30 mmol) of crude product of the compound according to Example XIX-1 are initially charged in 200 ml of anhydrous acetone, and 6.42 g (46.5 mmol) of potassium carbonate and 19.5 g (139.5 mmol) of methyl iodide are added. The mixture is stirred under reflux for 16 h.

The mixture is filtered and concentrated. The residue is purified by silica gel chromatography (dichloromethane:petroleum ether, 4:1→dichloromethane→dichloromethane: ethyl acetate, 30:1→10:1)

Yield: 4.6 g (16% of theory), oil $^1$H-NMR (400 MHz, $d_6$-DMSO):

δ=1.03 (s, 6H, 2—$CH_3$—C-aliph.), 2.32 (s, 3H, $CH_3$—C-arom.) 7.50 (d, 2H, Ar-H.), 7.81 (d, 2H, Ar—H) ppm.

Example XIX-1

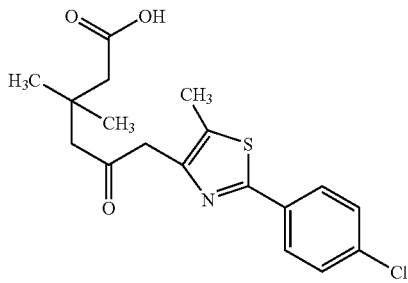

A solution of 12.7 g (45 mmol) of methyl 4-[2-(4-chlorophenyl)-5-methyl]-thiazolyl-acetate in 15 ml of anhydrous tetrahydrofuran is, at −15° C., added dropwise to a solution of 25 ml of LDA solution (2 molar) in 50 ml of anhydrous tetrahydrofuran, and the mixture is stirred at 0° C. for 60 min.

At −15° C., a solution of 4.26 g (30 mmol) of 3,3-dimethylglutaric anhydride in 10 ml of tetrahydrofuran is then added dropwise.

The solution is stirred at room temperature for 2 hours, 75 ml of water and 20 g of ammonium chloride are then added and the mixture is then acidified using concentrated hydrochloric acid.

The intermediate is extracted with ether and the solvent is distilled off. The residue is boiled under reflux with 25 g of potassium hydroxide and 170 ml of water for one day.

The mixture is cooled, acidified with concentrated hydrochloric acid and extracted with ether. The crude product is directly, without purification, reacted further.

Yield: 17 g (100% of theory), oil

The following compounds of the formula (III) were obtained analogously to Example (III-1) and in accordance with the general statements about the preparation:

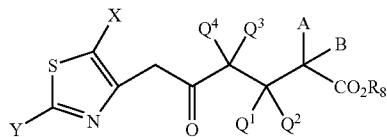

(III)

| Ex. No. | X | Y | A | B | Q¹ | Q² | Q³ | Q⁴ | R⁸ | m.p.° C. |
|---|---|---|---|---|---|---|---|---|---|---|
| III-2 | $CH_3$ | 4-Cl—$C_6H_4$ | H | H | H | H | H | H | $CH_3$ | oil |
| III-3 | $CH_3$ | 4-Cl—$C_6H_4$ | $CH_3$ | $CH_3$ | H | H | H | H | $CH_3$ | oil |
| III-4 | $CH_3$ | 4-Cl—$C_6H_4$ | H | H | —$(CH_2)_4$— | | H | H | $CH_3$ | oil |
| III-5 | $CH_3$ | 4-Cl—$C_6H_4$ | H | H | 4-Cl—$C_6H_4$ | H | H | H | $CH_3$ | oil |

The following compounds of the formula (XIX) were obtained analogously to Example (XIX-1) and in accordance with the general statements about the preparation:

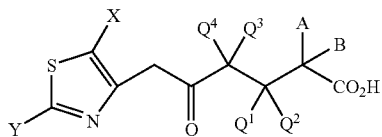

(XIX)

| Ex. No. | X | Y | A | B | Q¹ | Q² | Q³ | Q⁴ | m.p.° C. |
|---|---|---|---|---|---|---|---|---|---|
| XIX-2 | $CH_3$ | 4-Cl—$C_6H_4$ | H | H | H | H | H | H | oil |
| XIX-3 | $CH_3$ | 4-Cl—$C_6H_4$ | $CH_3$ | $CH_3$ | H | H | H | H | oil |
| XIX-4 | $CH_3$ | 4-Cl—$C_6H_4$ | H | H | —$(CH_2)_4$— | | H | H | oil |
| XIX-5 | $CH_3$ | 4-Cl—$C_6H_4$ | H | H | 4-Cl—$C_6H_4$ | H | H | H | oil |

Use Examples

Example A

*Meloidogyne* Test

Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate the plants develop. On the roots, galls are formed.

After the desired period of time, the nematicidal action is determined in % by the gall formation. 100% means that no galls have been found; 0% means that the number of galls on the treated plants corresponds to that of the untreated control.

In this test, for example, the following compounds of the preparation examples showed good activity:

| Active compounds | Concentration of active compound in ppm | Kill rate in % after 14 d |
|---|---|---|
| Ex. I-1-c-3 | 20 | 100 |
| Ex. I-1-a-1 | 20 | 95 |

Example B

*Myzus* Test (Systemic Action)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Savoy cabbage (*Brassica oleracea*) which is heavily infested by the green peach aphid (*Myzus persicae*) is watered with in each case 10 ml of preparation of active compound of the desired concentration such that the preparation of active compound penetrates into the soil without wetting the seedling. The active compound is taken up by the roots and transferred into the seedling.

After the desired period of time, the kill in % is determined. 100% means that all aphids have been killed; 0% means that none of the aphids have been killed.

In this test, for example, the following compounds of the preparation examples show good activity:

| Active compounds | Concentration of active compound in ppm | Kill rate in % after 10 d |
|---|---|---|
| Ex. I-1-c-2 | 20 | 95 |

Example C

*Phaedon* Larvae Test
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the preparation examples show good activity:

| Active compounds | Concentration of active compound in ppm | Kill rate in % after 7 d |
|---|---|---|
| Ex. I-1-c-1 | 500 | 100 |
| Ex. I-2-c-1 | 500 | 100 |

Example D

*Spodoptera Frugiperda* Test
Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillar larvae have been killed; 0% means that none of the caterpillar have been killed.

In this test, for example, the following compounds of the preparation examples show good activity:

| Active compound | Concentration of active compound in ppm | Kill rate in % after 7 d |
|---|---|---|
| Ex. I-1-a-2 | 500 | 100 |
| Ex. I-2-a-1 | 500 | 100 |
| Ex. I-1-c-1 | 500 | 100 |
| Ex. I-2-c-1 | 500 | 100 |

Example E

*Tetranychus* test (OP-Resistant/Dip Treatment)
Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites have been killed.

In this test, for example, the following compounds of the preparation examples show good activity:

| Active compound | Concentration of active compound in ppm | Kill rate in % after 7 d |
|---|---|---|
| Ex. I-1-c-3 | 100 | 98 |
| Ex. I-1-a-1 | 100 | 100 |
| Ex. I-2-a-2 | 100 | 99 |
| Ex. I-2-a-1 | 100 | 98 |
| Ex. I-1-c-1 | 100 | 95 |
| Ex. I-2-c-1 | 100 | 100 |

Example F1

Post-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0% =no effect (like untreated control)
100% =total destruction

Example F2

Pre-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:
0% = no effect (like untreated control)
100% = total destruction

| Post-emergence/ Greenhouse | g.a.i./ ha | Alopecurus | Avena fatua | Setaria | Sinapis |
|---|---|---|---|---|---|
| I-1-a-2 | 250 | 90 | 100 | 100 | 80 |
| I-1-a-3 | 250 | 90 | 100 | 100 | 80 |
| I-1-c-3 | 250 | 100 | 100 | 100 | 80 |
| I-1-a-1 | 250 | 100 | 100 | 100 | 70 |

| Post-emergence/ Greenhouse | g.a.i./ ha | Sugar-beet | Alopecurus | Avena fatua | Echinochloa | Setaria |
|---|---|---|---|---|---|---|
| I-2-a-1 | 250 | 0 | 90 | 95 | 100 | 100 |

| Post-emergence/ Greenhouse | g.a.i./ ha | Sugar-beet | Avena fatua | Echinochloa | Setaria | Sinapis |
|---|---|---|---|---|---|---|
| I-1-c-1 | 250 | 0 | 90 | 100 | 100 | 70 |

| Post-emergence/ Greenhouse | g.a.i./ ha | Alopecurus | Avena fatua | Setaria | Galium |
|---|---|---|---|---|---|
| I-2-c-1 | 250 | 90 | 100 | 100 | 80 |

| pre-emergence/ greenhouse | g a.i./ha | Wheat | Soya bean | Digitaria | Lolium | Setaria | Matricana |
|---|---|---|---|---|---|---|---|
| I-1-a-2 | 60 | 0 | 0 | 100 | 100 | 100 | 95 |

| pre-emergence/ greenhouse | g a.i./ha | Sugar beet | Alopercurus | Avena fatua | Digitaria | Polygonum |
|---|---|---|---|---|---|---|
| I-1-a-3 | 125 | 0 | 95 | 100 | 100 | 100 |

| pre-emergence/ greenhouse | g.a.i./ ha | Oilseed rape | Alopecurus | Digitaria | Lolium | Stellaria |
|---|---|---|---|---|---|---|
| I-1-c-2 | 125 | 0 | 95 | 100 | 100 | 100 |

| pre-emergence/ greenhouse | g.a.i./ ha | Wheat | Soya bean | Alopecurus | Lolium | Setaria | Stellaria |
|---|---|---|---|---|---|---|---|
| I-1-c-3 | 125 | 10 | 0 | 95 | 100 | 100 | 70 |

| pre-emergence/ greenhouse | g.a.i./ ha | Soya-bean | Lolium | Setaria | Matricaria | Stellaria |
|---|---|---|---|---|---|---|
| I-1-a-1 | 125 | 0 | 100 | 100 | 100 | 100 |

| pre-emergence/ greenhouse | g.a.i./ ha | Soya-bean | Bromus | Lolium | Setaria | Abutilon |
|---|---|---|---|---|---|---|
| I-2-a-1 | 125 | 0 | 95 | 100 | 100 | 70 |

Example G

In vitro test for the $ED_{50}$ determination in microorganisms

A methanolic solution of the active compound to be tested, admixed with the emulsifier PS16, is pipetted into the wells of microtitre plates. After the solvent has evaporated, 200 µl of potato/dextrose medium are added to each well.

Beforehand, a suitable concentration of spores or mycelium of the fungus to be tested was added to the medium.

The resulting concentrations of the active compound are 0.1, 1, 10 and 100 ppm. The resulting concentration of the emulsifier is 300 ppm.

The plates are then incubated on a shaker at a temperature of 22° C. for 3-5 days, until sufficient growth can be observed in the untreated control.

Evaluation is carried out photometrically at a wavelength of 620 nm. The dose of active compound which causes a 50% inhibition of fungal growth compared to the untreated control ($ED_{50}$) is calculated from the data measured at different concentrations.

| Active compound | Microorganism | $ED_{50}$ value |
|---|---|---|
| Ex. I-1-a-2 | Pyricularia oryzae | <0.1 |
|  | Septoria tritici | <0.1 |
|  | Ustilago avenae | <0.1 |
| Ex. I-2-a-2 | Pyricularia oryzae | 1.96 |
|  | Septoria tritici | <0.1 |
|  | Ustilago avenae | <0.1 |
| Ex. I-2-a-3 | Pyricularia oryzae | <0.1 |
|  | Septoria tritici | <0.1 |
|  | Ustilago avenae | 0.1 |

Example H

*Sphaerotheca* Test (Cucumber)/Protective
Solvent: 24.5 parts by weight of acetone 24.5 parts by weight of dimethylacetamide
Emulsifier: 1 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

| Active compound | Application rate of active compound in g/ha | % efficacy |
|---|---|---|
| Ex. I-1-a-2 | 100 | 100 |

Example I

*Venturia* Test (Apple)/Protective
Solvent: 24.5 parts by weight of acetone 24. 5 parts by weight of dimethylacetamide
Emulsifier: 1 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

| Active compound | Application rate of active compound in g/ha | % efficacy |
|---|---|---|
| Ex. I-1-a-2 | 100 | 91 |

Example J

*Alternaria* Test (Tomato)/Protective
Solvent: 24.5 parts by weight of acetone 24.5 parts by weight of dimethylacetamide
Emulsifier: 1 part by weight of alkyl-arylpolyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Alternaria solani*. The plants are then placed in an incubation cabin at about 200° C. and 100% relative atmospheric humidity.

Evaluation is carried out 3 days after the inoculation. 0% means an efficacy which corresponds to that of the control, whereas an efficacy of 100% means that no infection is observed.

| Active compound | Application rate of active compound in g/ha | % efficacy |
|---|---|---|
| Ex. I-1-a-2 | 100 | 93 |

Example K

*Botrytis* Test (Bean)/Protective
Solvent: 24.5 parts by weight of acetone 24.5 parts by weight of dimethylacetamide
Emulsifier: 1 part by weight of alkyl-arylpolyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, two small pieces of agar colonized by *Botrytis cinerea* are placed onto each leaf. The inoculated plants are placed in a dark chamber at about 20° C. and 100% relative atmospheric humidity.

2 days after the inoculation, the size of the infested areas on the leaves is evaluated. 0% means an efficacy which corresponds to that of the control, whereas an efficacy of 100% means that no infection is observed.

| Active compound | Application rate of active compound in g/ha | % efficacy |
|---|---|---|
| Ex. I-1-a-2 | 500 | 92 |

Example L

Critical Concentration Test/Soil Insects-Treatment of Transgenic Plants
Test insect: *Diabrotica balteata*—larvae in soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. The concentration of the active compound in the preparation is virtually immaterial, only the amount by weight of active compound per volume unit of soil, which is stated in ppm (mg/l) matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the corresponding test insects are placed into the treated soil. After a further 7 days, the efficacy of the active compound is determined by counting the number of maize plants that emerged (1 plant=20% activity).

Example M

*Heliothis Virescens* Test—Treatment of Transgenic Plants
Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trademark of Monsanto Comp., USA) are treated by being dipped into the preparation of active compound of the desired concentration and are populated with the tobacco budworm caterpillar *Heliothis virescens* while the leaves are still moist.

After the desired period of time, the kill of the insects is determined.

The invention claimed is:
1. A compounds of the Formula (I)

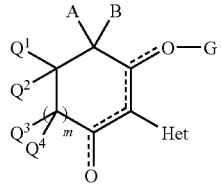

in which
Het represents

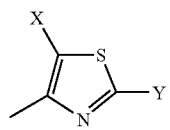

X represents hydrogen, halogen, $C_1$-$C_6$ alkyl, $C_1$-$C_6$ alkoxy, $C_3$-$C_6$ alkenyloxy, nitro or cyano,
Y represents halogen, $C_1$-$C_6$ alkyl, $C_1$-$C_6$ halogenoalkyl, $C_1$-$C_6$-alkoxy, $C_1$-$C_6$-halogenoalkoxy or represents the groups

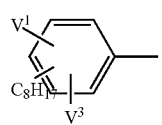 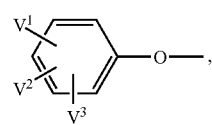

m represents the number 0 or 1,

A represents hydrogen, or represents in each case optionally halogen-substituted alkyl, alkenyl, alkoxyalkyl, polyalkoxyalkyl, alkylthioalkyl, saturated or unsaturated, optionally substituted cycloalkyl in which optionally at least one ring atom is replaced by a heteroatom, or in each case optionally halogen-, alkyl-, halogenoalkyl-, alkoxy-, halogenoalkoxy-, cyano- or nitro-substituted aryl, arylalkyl or hetaryl, B represents hydrogen or alkyl or, A and B together with the carbon atom to which they are attached represent a saturated or unsaturated, unsubstituted or substituted cycle which optionally contains at least one heteroatom, A and $Q^1$ together represent optionally substituted alkanediyl in which two not directly adjacent carbon atoms optionally form a further optionally substituted cycle, or $Q^1$ represents hydrogen, alkyl, alkoxyalkyl, optionally substituted cycloalkyl (in which optionally one methylene group is replaced by oxygen or sulphur) or in each case optionally substituted phenyl, hetaryl, phenylalkyl or hetarylalkyl, $Q^2$, $Q^3$, $Q^4$ independently of one another represent hydrogen or alkyl, or $Q^1$ and $Q^2$ together with the carbon atom to which they are attached represent a saturated or unsaturated, unsubstituted or substituted cycle which optionally contains one heteroatom, G represents hydrogen (a) or represents one of the groups

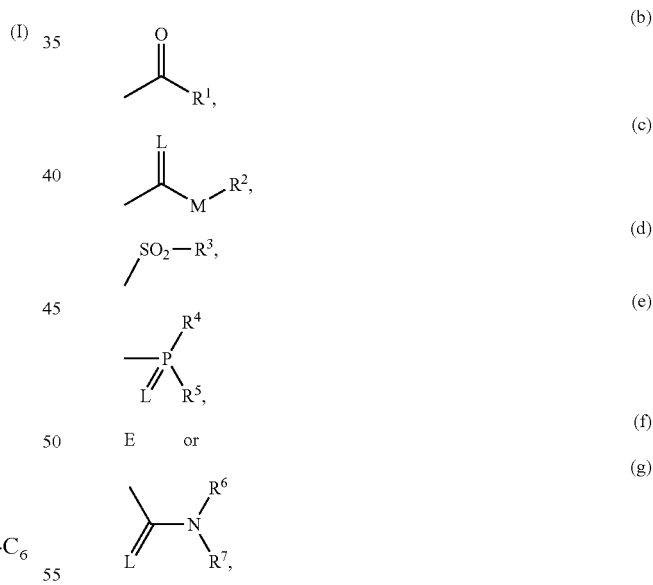

in which
E represents a metal ion or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, R² represents in each case optionally halogen-substituted alkyl, alkenyl, alkoxyalkyl, polyalkoxyalkyl or represents in each case optionally substituted cycloalkyl, phenyl or benzyl, R³ represents in each case optionally substituted alkyl, halogenoalkyl, phenyl or benzyl, R⁴ and R⁵ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, R⁶ and R⁷ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur.

2. A compound of the Formula (I) according to claim 1, in which

Het represents

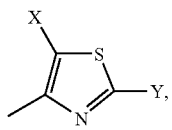

m represents the number 0 or 1,

X represents hydrogen, halogen, $C_1$-$C_6$-alkyl, $C_1$-$C_6$-alkoxy, $C_3$-$C_6$-alkenyloxy, nitro or cyano, Y represents halogen, $C_1$-$C_6$-alkyl, $C_1$-$C_6$-halogenoalkyl, $C_1$-$C_6$-alkoxy, $C_1$-$C_6$-halogenoalkoxy or represents the groups

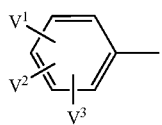 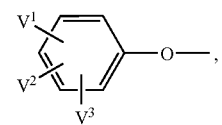

V¹ represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-halogenoalkyl, $C_1$-$C_4$-halogenoalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally mono- or polysubstituted by halogen, $C_1$-$C_6$-alkyl, $C_1$-$C_6$-alkoxy, $C_1$-$C_4$-halogenoalkyl, $C_1$-$C_4$-halogenoalkoxy, nitro or cyano, V² and V³ independently of one another represent hydrogen, halogen, $C_1$-$C_6$-alkyl, $C_1$-$C_6$-alkoxy, $C_1$-$C_4$-halogenoalkyl or $C_1$-$C_4$-halogeno-alkoxy, V¹ and V² jointly together with the carbon atoms to which they are attached represent an optionally $C_1$-$C_4$-alkyl- or halogen-substituted 5- or 6-membered cycle in which optionally one or two carbon atoms may be replaced by oxygen, sulphur or nitrogen, A represents hydrogen or in each case optionally halogen-substituted $C_1$-$C_{12}$-alkyl, $C_3$-$C_8$-alkenyl, $C_1$-$C_6$-alkoxy-$C_1$-$C_4$-alkyl, optionally halogen-, $C_1$-$C_4$-alkyl- or $C_1$-$C_4$-alkoxy-substituted $C_3$-$C_8$-cycloalkyl or $C_3$-$C_6$-cycloalkyl-$C_1$-$C_4$-alkyl, in which optionally one or two not directly adjacent ring members are replaced by oxygen and/or sulphur, or represents in each case optionally halogen-, $C_1$-$C_6$-alkyl-, $C_1$-$C_6$-halogenoalkyl-, $C_1$-$C_6$-alkoxy-, $C_1$-$C_6$-halogenoalkoxy-, cyano- or nitro-substituted phenyl, benzyl, hetaryl having 5 or 6 ring atoms or hetaryl-$C_1$-$C_4$-alkyl having 5 or 6 ring atoms, B represents hydrogen or $C_1$-$C_6$-alkyl, A, B and the carbon atom to which they are attached represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_6$-alkyl, $C_3$-$C_8$-cycloalkyl, $C_1$-$C_6$-halogenoalkyl, $C_1$-$C_6$-alkoxy, $C_1$-$C_6$-alkylthio, halogen or phenyl, A and Q¹ together represent $C_3$-$C_6$-alkanediyl which is optionally mono- or disubstituted by identical or different substituents from the group consisting of $C_1$-$C_4$-alkyl and $C_1$-$C_4$-alkoxy, Q¹ represents hydrogen, $C_1$-$C_6$-alkyl, $C_1$-$C_6$-alkoxy-$C_1$-$C_2$-alkyl, optionally fluorine-, chlorine-, $C_1$-$C_4$-alkyl-, $C_1$-$C_2$-halogenoalkyl- or $C_1$-$C_4$-alkoxy-substituted $C_3$-$C_8$-cycloalkyl in which optionally one methylene group is replaced by oxygen or sulphur or in each case optionally halogen-, $C_1$-$C_4$-alkyl-, $C_1$-$C_4$-alkoxy-, $C_1$-$C_2$-halogenoalkyl-, $C_1$-$C_2$-halogenoalkoxy-, cyano- or nitro-substituted phenyl, pyridyl, thienyl, thiazolyl, phenyl-$C_1$-$C_4$-alkyl, pyridyl-$C_1$-$C_2$-alkyl or thiazolyl-$C_1$-$C_2$-alkyl, Q², Q³, Q⁴ independently of one another represent hydrogen or $C_1$-$C_4$-alkyl, Q¹ and Q² together with the carbon atom to which they are attached represent optionally $C_1$-$C_6$-alkyl-, $C_1$-$C_6$-alkoxy- or $C_1$-$C_2$-halogenoalkyl-substituted $C_3$-$C_7$-cycloalkyl in which optionally one ring member is replaced by oxygen or sulphur, G represents hydrogen (a) or represents one of the groups (b) 

(c) 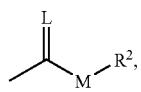

(d) 

(e) 

(f) E or (g) 

in which

E represents a metal ion or an ammonium ion,

L represents oxygen or sulphur and

M represents oxygen or sulphur,

R¹ represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$- alkoxy-$C_1$-$C_8$-alkyl or optinally halogen-, $C_1$-$C_6$-alkyl- or $C_1$-$C_6$-alkoxy-substituted $C_3$-$C_8$-cycloalkyl, in which optionally one or more not directly adjacent ring members are replaced by oxygen and/or sulphur, represents optionally halogen-, cyano-, nitro-, $C_1$-$C_6$-alkyl, $C_1$-$C_6$-alkoxy-, $C_1$-$C_6$-halogenoalkyl-, $C_1$-$C_6$-halogenoalkoxy-, $C_1$-$C_6$-alkylthio or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-halogenoalkyl- or $C_1$-$C_6$-halogenoalkoxy-substituted phenyl-$C_1$-$C_6$-alkyl, represents optionally halogen-, $C_1$-$C_6$-alkyl- or trifluoromethyl-substituted 5- or 6-membered hetaryl, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl, $R^2$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-halogenoalkyl- or $C_1$-$C_6$-halogenoalkoxy-substituted phenyl or benzyl, $R^3$ represents optionally halogeno-substituted $C_1$-$C_8$-alkyl or represents in each case optionally halogen-, $C_1$-$C_6$-alkyl-, $C_1$-$C_6$-alkoxy-, $C_1$-$C_4$-halogenoalkyl-, $C_1$-$C_4$-halogenoalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-halogenoalkoxy-, $C_1$-$C_4$-alkylthio-, $C_1$-$C_4$-halogenoalkylthio-, $C_1$-$C_4$-alkyl- or $C_1$-$C_4$-halogenoalkyl-substituted phenyl, benzyl, phenoxy or phenylthio, $R^6$ and $R^7$ independently of one another represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-halogenoalkyl-, $C_1$-$C_8$-alkyl- or $C_1$-$C_8$-alkoxy-substituted phenyl, optionally halogen-, $C_1$-$C_8$-alkyl-, $C_1$-$C_8$-halogenoalkyl- or $C_1$-$C_8$-alkoxy-substituted benzyl or together with the nitrogen to which they are attached represent an optionally $C_1$-$C_4$-alkyl-substituted $C_3$-$C_6$-alkylene radical in which optionally one carbon atom is replaced by oxygen or sulphur.

3. A compound of the Formula (I) according to claim 1, in which

Het represents

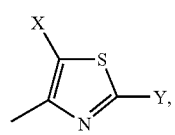

m represents the number 0 or 1,

X represents hydrogen, chlorine, bromine or $C_1$-$C_4$-alkyl,

Y represents chlorine, bromine, $C_1$-$C_4$-alkyl, $C_1$-$C_4$-halogenoalkyl, $C_1$-$C_4$-alkoxy, $C_1$-$C_4$-halogenoalkoxy or the group

$V^1$ represents hydrogen, fluorine, chlorine, $C_1$-$C_6$-alkyl, $C_1$-$C_4$-alkoxy, $C_1$-$C_2$-halogenoalkyl, $C_1$-$C_2$-halogenoalkoxy, nitro, cyano or phenoxy which is optionally mono- or disubstituted by fluorine, chlorine, bromine, $C_1$-$C_4$-alkyl, $C_1$-$C_4$-alkoxy, $C_1$-$C_2$-halogenoalkyl, $C_1$-$C_2$-halogenoalkoxy, nitro or cyano, $V^2$ represents hydrogen, fluorine, chlorine, bromine, $C_1$-$C_4$-alkyl, $C_1$-$C_4$-alkoxy, $C_1$-$C_2$-halogenoalkyl or $C_1$-$C_2$-halogenoalkoxy, $V^1$ and $V^2$ jointly, together with the carbon atoms to which they are attached, represent an optionally fluorine- or methyl-substituted 5- or 6-membered cycle in which optionally one or two carbon atoms may be replaced by oxygen, A represents hydrogen, represents $C_1$-$C_8$-alkyl or $C_1$-$C_4$-alkoxy-$C_1$-$C_2$-alkyl, each of which is optionally mono- to trisubstituted by fluorine, represents $C_5$-$C_6$-cycloalkyl or $C_3$-$C_6$-cycloalkyl-$C_1$-$C_2$-alkyl in which optionally one ring member is replaced by oxygen or sulphur, each of which radicals is optionally mono- or disubstituted by fluorine, chlorine, methyl, ethyl or methoxy, or represents phenyl or benzyl, each of which is optionally mono- or disubstituted by fluorine, chlorine, bromine, $C_1$-$C_4$-alkyl, $C_1$-$C_2$-halogenoalkyl, $C_1$-$C_4$-alkoxy or $C_1$-$C_2$-halogenoalkoxy, B represents hydrogen or $C_1$-$C_4$-alkyl, A, B and the carbon atom to which they are attached represent saturated $C_5$-$C_6$-cycloalkyl in which optionally one ring member is replaced by oxygen and which is optionally monosubstituted by $C_1$-$C_4$-alkyl, trifluoromethyl or $C_1$-$C_4$-alkoxy, with the proviso that in this case $Q^1$ represents only hydrogen or $C_1$-$C_4$-alkyl, A and $Q^1$ together represent $C_3$-$C_4$-alkanediyl which is optionally mono- or disubstituted by methyl, ethyl, methoxy or ethoxy, $Q^1$ represents hydrogen, $C_1$-$C_4$-alkyl, $C_1$-$C_4$-alkoxy-$C_1$-$C_2$-alkyl, or optionally methyl- or methoxy-substituted $C_3$-$C_6$-cycloalkyl, in which optionally one methylene group is replaced by oxygen, or represents phenyl or benzyl, each of which is optionally mono- or disubstituted by fluorine, chlorine, bromine, $C_1$-$C_4$-alkyl, $C_1$-$C_4$-alkoxy, trifluoromethyl or trifluoromethoxy, $Q^2$, $Q^3$, $Q^4$ independently of one another represent hydrogen, methyl or ethyl, $Q^1$ and $Q^2$ together with the carbon atom to which they are attached represent optionally $C_1$-$C_4$-alkyl- or $C_1$-$C_4$-alkoxy-substituted saturated $C_5$-$C_6$-cycloalkyl in which optionally one ring member is replaced by oxygen, with the proviso that in this case A only represents hydrogen or $C_1$-$C_4$-alkyl, G represents hydrogen (a) or represents one of the groups

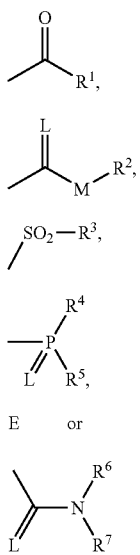

(b)
(c)
(d)
(e)
(f)
(g)

in which
E represents a metal ion or an ammonium ion,
L represents oxygen or sulphur and
M represents oxygen or sulphur,
R$^1$ represents C$_1$-C$_{16}$-alkyl, C$_2$-C$_{16}$-alkenyl, C$_1$-C$_4$-alkoxy-C$_1$-C$_2$-alkyl, C$_1$-C$_4$-alkylthio-C$_1$-C$_2$-alkyl, each of which is optionally mono- to pentasubstituted by fluorine or chlorine, or C$_3$-C$_6$-cycloalkyl in which optionally one or two not directly adjacent ring members are replaced by oxygen and/or sulphur and which is optionally mono- or disubstituted by fluorine, chlorine, C$_1$-C$_4$-alkyl or C$_1$-C$_5$-alkoxy,
represents phenyl which is optionally mono- or disubstituted by fluorine, chlorine, bromine, cyano, nitro, C$_1$-C$_4$-alkyl, C$_1$-C$_4$-alkoxy, trifluoromethyl or trifluoromethoxy,
represents pyridyl or thienyl, each of which is optionally monosubstituted by fluorine, chlorine, bromine, methyl, ethyl or trifluoromethyl,
R$^2$ represents C$_1$-C$_{16}$-alkyl, C$_2$-C$_{16}$-alkenyl or C$_1$-C$_4$-alkoxy-C$_2$-C$_4$-alkyl,
represents C$_3$-C$_6$-cycloalkyl which is optionally mono- or disubstituted by methyl, ethyl or methoxy,
represents phenyl or benzyl, each of which is optionally mono- or disubstituted by fluorine, chlorine, bromine, cyano, nitro, C$_1$-C$_4$-alkyl, C$_1$-C$_4$-alkoxy, trifluoromethyl or trifluoromethoxy,
R$^3$ represents C$_1$-C$_4$-alkyl which is optionally mono- to pentasubstituted by fluorine or represents phenyl which is optionally mono- or disubstituted by fluorine, chlorine, bromine, C$_1$-C$_4$-alkyl, C$_1$-C$_4$-alkoxy, trifluoromethyl, trifluoromethoxy, cyano or nitro,
R$^4$ represents C$_1$-C$_6$-alkyl, C$_1$-C$_6$-alkoxy, C$_1$-C$_6$-alkylamino, di-(C$_1$-C$_6$-alkyl)amino, C$_1$-C$_6$-alkylthio, or represents phenyl, benzyl, phenoxy or phenylthio, each of which is optionally mono- or disubstituted by fluorine, chlorine, bromine, nitro, cyano, C$_1$-C$_3$-alkoxy, trifluoromethoxy, C$_1$-C$_3$-alkyl or trifluoromethyl,
R$^5$ represents C$_1$-C$_4$-alkyl, C$_1$-C$_4$-alkoxy or C$_1$-C$_4$-alkylthio,
R$^6$ represents hydrogen, C$_1$-C$_6$-alkyl, C$_3$-C$_6$-cycloalkyl, C$_1$-C$_6$-alkoxy, C$_3$-C$_6$-alkenyl, C$_1$-C$_6$-alkoxy-C$_1$-C$_6$-alkyl, represents phenyl which is optionally mono- or disubstituted by fluorine, chlorine, bromine, trifluoromethyl, C$_1$-C$_4$-alkyl or C$_1$-C$_4$-alkoxy, represents benzyl which is optionally substituted by fluorine, chlorine, bromine, methyl, ethyl, trifluoromethyl or methoxy,
R$^7$ represents hydrogen, C$_1$-C$_6$-alkyl or C$_3$-C$_6$-alkenyl,
R$^6$ and R$^7$ together with nitrogen atom to which they are attached represent a C$_5$-C$_6$-alkylene radical in which optionally one methylene group is replaced by oxygen or sulphur and which is optionally mono- or disubstituted by methyl or ethyl.

4. A compound of the Formula (I) according to claim 1, in which
Het represents

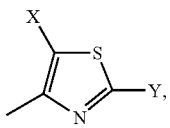

m represents the number 0 or 1,
X represents hydrogen, chlorine, bromine, methyl, ethyl, n-propyl or isopropyl,
Y represents the group

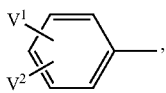

V$^1$ represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy or 4-chlorophenoxy,
V$^2$ represents hydrogen, fluorine, chlorine, bromine, methyl, methoxy or trifluoromethyl,
A represents hydrogen, methyl, ethyl, n-propyl, isopropyl, n-butyl, isobutyl, tert-butyl, methoxymethyl, ethoxymethyl, phenyl or cyclohexyl,
B represents hydrogen, methyl or ethyl,
A, B and the carbon atom to which they are attached represent saturated C$_5$-C$_6$-cycloalkyl in which optionally one ring member is replaced by oxygen and which is optionally monosubstituted by methyl, ethyl, n-propyl, isopropyl, n-butyl, isobutyl, tert-butyl, trifluoromethyl, methoxy, ethoxy, n-propoxy, n-butoxy or isobutoxy,
with the provisio that in this case Q$^1$ only represents hydrogen,
A and Q$^1$ together represent C$_3$-C$_4$-alkanediyl,
Q$^1$ represents hydrogen, methyl, ethyl, n-propyl, isopropyl, cyclopropyl, cyclopentyl, cyclohexyl or 4-chlorophenyl,
Q$^2$, Q$^3$, Q$^4$ independently of one another represent hydrogen, methyl or ethyl,
Q$^1$ and Q$^2$ together with the carbon atom to which they are attached represent optionally methyl-, ethyl-, methoxy-, ethoxy-, n-propoxy- or n-butoxy-substituted saturated C$_5$-C$_6$-cycloalkyl in which optionalloy one ring member is replaced by oxygen,
with the proviso that in this case A only represents hydrogen, G represents hydrogen (a) or represents one of the groups

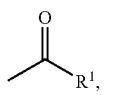
(b)

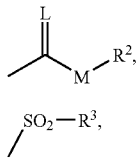
(c)

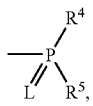
(d)

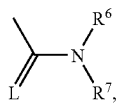
(e)

E or (f)

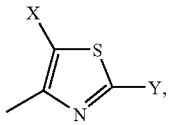
(g)

in which
E represents a metal ion or an ammonium ion,
L represents oxygen or sulphur and
M represents oxygen or sulphur,
$R^1$ represents in each case optionally fluorine- or chlorine-substituted $C_1$-$C_8$-alkyl, $C_2$-$C_8$-alkenyl, $C_1$-$C_2$-alkoxy-$C_1$-$C_2$-alkyl, $C_1$-$C_2$-alkylthio-$C_1$-$C_2$-alkyl or cyclopropyl or cyclohexyl, each of which is optionally monosubstituted by fluorine, chlorine, methyl, ethyl or methoxy,
represents phenyl which is optionally monosubstituted by fluorine, chlorine, bromine, cyano, nitro, methyl, ethyl, isopropyl, tert-butyl, methoxy, trifluoromethyl or trifluoromethoxy,
represents thienyl or pyridyl, each of which is optionally monosubstituted by fluorine, chlorine, bromine or methyl,
$R^2$ represents $C_1$-$C_8$-alkyl, $C_2$-$C_8$-alkenyl or $C_1$-$C_4$-alkoxy-$C_2$-alkyl,
represents $C_3$-$C_6$-cycloalkyl which is optionally monosubstituted by methyl, ethyl or methoxy,
represents phenyl or benzyl, each of which is optionally monosubstituted by fluorine, chlorine, cyano, nitro, methyl, ethyl, isopropyl, tert-butyl, methoxy, trifluoromethyl or trifluoromethoxy,
$R^3$ represents methyl or ethyl, each of which is optionally trisubstituted by fluorine or represents phenyl which is optionally monosubstituted by fluorine, chlorine, bromine, methyl, tert-butyl, methoxy, trifluoromethyl, trifluoromethoxy, cyano or nitro,
$R^4$ represents $C_1$-$C_4$-alkyl, $C_1$-$C_4$-alkoxy, $C_1$-$C_4$-alkylamino, di-($C_1$-$C_4$-alkyl)amino, $C_1$-$C_4$-alkylthio or represents phenyl, phenoxy or phenylthio, each of which is optionally monosubstituted by fluorine, chlorine, bromine, nitro, cyano, $C_1$-$C_2$-alkoxy, trifluoromethoxy or $C_1$-$C_3$-alkyl,
$R^5$ represents methyl, ethyl, methoxy, ethoxy, methylthio or ethylthio,
$R^6$ represents hydrogen, represents $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_1$-$C_4$-alkyl, $R^7$ represents hydrogen, $C_1$-$C_4$-alkyl or $C_3$-$C_4$-alkenyl,
$R^6$ and $R^7$ together with the nitrogen atom to which they are attached represent a $C_5$-alkylene radical in which optionally one methylene group is replaced by oxygen.

5. A compound of the Formula (I) according to claim 1, in which
Het represents

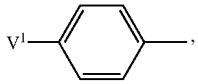

m represents the number 0 or 1,
X represents hydrogen, methyl or ethyl,
Y represents the group

, $V^1$ represents hydrogen, chlorine, methyl, ethyl, n-propyl, isopropyl, n-butyl, isobutyl, tert-butyl, trifluoromethyl or represents 4-chloro-phenoxy,
A represents hydrogen, methyl, ethyl, n-propyl, isopropyl, n-butyl, isobutyl, phenyl or cyclohexyl,
B represents hydrogen, methyl or ethyl,
A, B and the carbon atom to which they are attached represent saturated $C_5$-$C_6$-cycloalkyl in which optionally one ring member is replaced by oxygen and which is optionally monosubstituted by methyl, ethyl, n-propyl, isopropyl, n-butyl, isobutyl, tert-butyl, methoxy, ethoxy, n-propoxy, n-butoxy or isobutoxy,
with the proviso that in this case $Q^1$ only represents hydrogen,
A and $Q^1$ together represent $C_3$-$C_4$-alkanediyl,
$Q^1$ represents hydrogen, methyl, ethyl, n-propyl, isopropyl or 4-chlorophenyl,
$Q^2$ represents hydrogen, methyl or ethyl,
$Q^3$ represents hydrogen,
$Q^4$ represents hydrogen,
$Q^1$ and $Q^2$ together with the carbon atom to which they are attached represent saturated $C_5$-$C_6$-cycloalkyl,
with the proviso that in this case A only represents hydrogen,
G represents hydrogen (a) or represents one of the groups

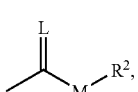
(b)

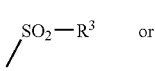
(c)

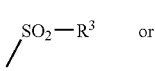or (d)

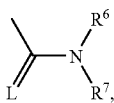
(g)

in which
L represents oxygen and
M represents oxygen or sulphur, $R^1$ represents $C_1$-$C_8$-alkyl, $C_1$-$C_2$-alkoxy-$C_1$-$C_2$-alkyl or cyclopropyl which is optionally monosubstituted by chlorine, represents phenyl which is optionally monosubstituted by chlorine, represents pyridyl which is optionally monosubstituted by chlorine, $R^2$ represents $C_1$-$C_8$-alkyl, represents phenyl or benzyl, $R^3$ represents methyl or ethyl, $R^6$ and $R^7$ together with the nitrogen atom to which they are attached represent a $C_5$-alkylene radical in which optionally one methylene group is replaced by oxygen.

6. A process for preparing a compound of the Formula (I) according to claim 1, wherein to obtain (A) a compound of the Formula (I-1-a)

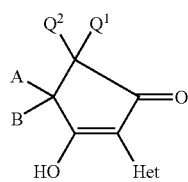
(I-1-a)

in which

A, B, $Q^1$, $Q^2$ and Het are as defined in claim 1, a compound of the Formula (II)

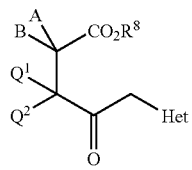
(II)

in which

A, B, $Q^1$, $Q^2$ and Het are as defined in claim 1 and $R^8$ represents alkyl, is condensed intramolecularly, optionally in the presence of a diluent and in the presence of a base, (B) a compound of the Formula (I-2-a)

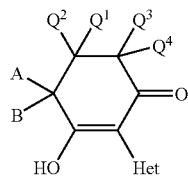
(I-2-a)

in which

A, B, $Q^1$, $Q^2$, $Q^3$, $Q^4$, and Het are as defined claim 1, a compound of the Formula (III)

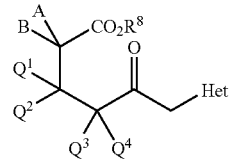
(III)

in which

A, B, $Q^1$, $Q^2$, $Q^3$, $Q^4$ and Het are as defined in claim 1 and $R^8$ represents alkyl, is condensed intramolecularly in the presence of a diluent and in the presence of a base, (C) a compound of the Formulae (I-1-b) or (I-2-b)

(I-1-b):

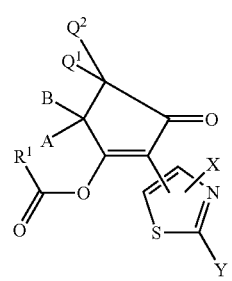

(I-2-b):

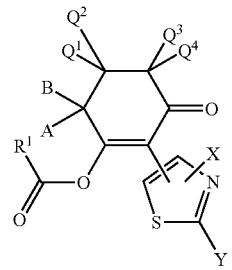

in which A, B, $Q^1$, $Q^2$, $Q^3$, $Q^4$, m, $R^1$ and Het are as defined in claim 1, a compound of the Formulae (I-1-a) or (I-2-a) shown above in which A, B, $Q^1$, $Q^2$, $Q^3$, $Q^4$, m and Het are as defined in claim 1 are in each case (α) reacted with an acid halide of the Formula (IV)

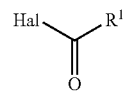
(IV)

in which $R^1$ is as defined in claim 1 and

Hal represents halogen or (β) reacted with a carboxylic anhydride of the Formula (V)

$R^1$—CO—O—CO—$R^1$ (V)

in which

R$^1$ is as defined in claim 1, optionally in the presence of a diluent and optionally in the presence of an acid binder;

(D) a compound of the Formulae (I-1-c) or (I-2-c)

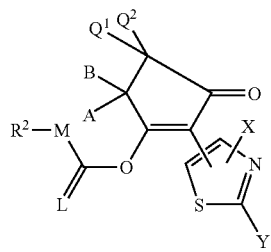
(I-1-c)

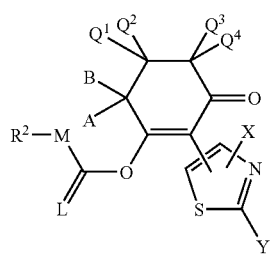
(I-2-c)

in which A, B, Q$^1$, Q$^2$, Q$^3$, Q$^4$, m, R$^2$, M and Het are as defined in claim 1 and L represents oxygen, compounds of the Formulae (I-1-a) or (I-2-a) shown above in which A, B, Q$^1$, Q$^2$, Q$^3$, Q$^4$, m and Het are as defined in claim 1 are in each case reacted with a chloroformic ester or a chloroformic thioester of the Formula (VI)

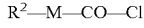
(VI)

in which

R$^2$ and M are as defined in claim 1, optionally in the presence of a diluent and optionally in the presence of an acid binder;

(E) a compound of the Formulae (I-1-c) or (I-2-c) shown above in which A, B, Q$^1$, Q$^2$, Q$^3$, Q$^4$, m, R$^2$, M and Het are as defined in claim 1 and L represents sulphur, compounds of the Formulae (I-1 -a) or (I-2-a) shown above in this claim 6 in which A, B, Q$^1$, Q$^2$, Q$^3$, Q$^4$, m and Het are as defined in claim 1 are in each case reacted with a chloromonothioformic ester or a chlorodithioformic ester of the Formula (VII)

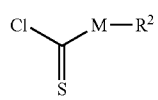
(VII)

in which

M and R$^2$ are as defined in claim 1, optionally in the presence of a diluent and optionally in the presence of an acid binder and (F) a compound of the Formulae (I-1-d) or (I-2-d)

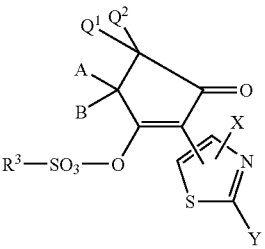
(I-1-d)

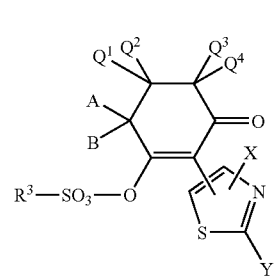
(I-2-d)

in which A, B, Q$^1$, Q$^2$, Q$^3$, Q$^4$, m, R$^3$ and Het are as defined in claim 1, compounds of the Formulae (I-1-a) or (I-2-a) shown above which A, B, Q$^1$, Q$^2$, Q$^3$, Q$^4$, m and Het are as defined in claim 1 are in each case reacted with a sulphonyl chloride of the Formula (VIII)

R$^3$—SO$_2$—Cl (VIII)

in which

R$^3$ is as defined in claim 1, optionally in the presence of a diluent and optionally in the presence of an acid binder, (G) a compound of the Formulae (I-1-e) or (I-2-e)

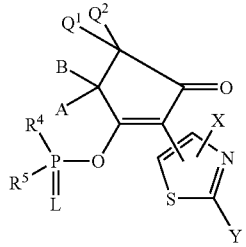
(I-1-e)

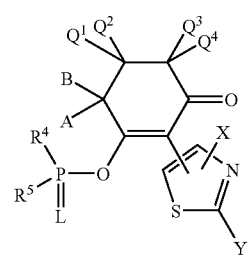
(I-2-e)

in which A, B, L, Q$^1$, Q$^2$, Q$^3$, Q$^4$, m, R$^4$, R$^5$ and Het are as defined in claim 1, compounds of the Formulae (I-1-a) or (I-2-a) shown above in which A, B, Q$^1$, Q$^2$, Q$^3$, Q$^4$, m and Het are as defined in claim 1 are in each case reacted with a phosphorus compound of the Formula (IX)

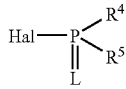 (IX)

in which
L, $R^4$ and $R^5$ are as defined in claim 1 and
Hal represents halogen,
optionally in the presence of a diluent and optionally in the presence of an acid binder, (H) a compound of the formulae (I-1-f) or (I-2-f)

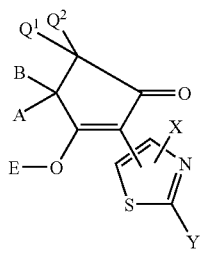 (I-1-f)

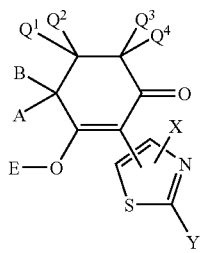 (I-2-f)

in which A, B, E, $Q^1$, $Q^2$, $Q^3$, $Q^4$, m and Het are as defined in claim 1, compounds of the Formulae (I-1-a) or (I-2-a) shown above in which A, B, $Q^1$, $Q^2$, $Q^3$, $Q^4$, m and Het are as defined in claim 1 are in each case
reacted with a metal compound or an amine of the Formulae (X) and (XI), respectively, $Me(OR^{11})_t$ (X)

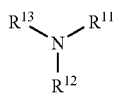 (XI)

in which
Me represents a mono- or divalent metal,
t represents the number 1 or 2 and
$R^{11}$, $R^{12}$, $R^{13}$ independently of one another represent hydrogen or alkyl,
optionally in the presence of a diluent, (I) a compound of the Formulae (I-1-g) or (I-2-g)

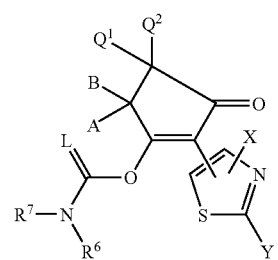 (I-1-g)

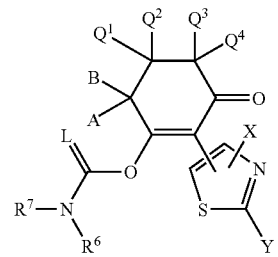 (I-2-g)

in which A, B, L, $Q^1$, $Q^2$, $Q^3$, $Q^4$, m, $R^6$, $R^7$ and Het are as defined in claim 1, compounds of the Formulae (I-1-a) or (I-2-a) shown above in which A, B, $Q^1$, $Q^2$, $Q^3$, $Q^4$, m and Het are as defined in claim 1 are in each case (α) reacted with an isocyanater or isothiocyanater of the Formula (XII)

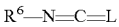
$R^6$—N=C=L (XII)

in which
$R^6$ and L are as defined in claim 1,
optionally in the presence of a diluent and optionally in the presence of a catalyst, or (β) reacted with a carbamoyl chloride or a thiocarbamoyl chloride of the Formula (XIII)

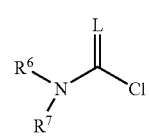 (XIII)

in which
L, $R^6$ and $R^7$ are as defined in claim 1,
optionally in the presence of a diluent and optionally in the presence of an acid binder.

7. A pesticide comprising at least one compound of the Formula (I) according to claim 1.

8. A method for controlling animal pests, undesirable vegetation and/or fungi comprising allowing a compound of the Formula (I) according to claim 1 to act on pests, undesirable vegetation and/or fungi and/or their habitat.

9. A process for preparing pesticides, herbicides and/or fungicides comprising mixing one or more compounds of the Formula (I) according to claim 1 with one or more extenders and/or surfactants.

* * * * *